(12) United States Patent
Chu et al.

(10) Patent No.: US 6,752,811 B2
(45) Date of Patent: Jun. 22, 2004

(54) LASER-RESISTANT MEDICAL RETRIEVAL DEVICE

(75) Inventors: Michael S. H. Chu, Brookline, MA (US); George Bourne, Southboro, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 39 days.

(21) Appl. No.: 09/988,442

(22) Filed: Nov. 20, 2001

(65) Prior Publication Data

US 2002/0068943 A1 Jun. 6, 2002

Related U.S. Application Data

(62) Division of application No. 09/398,322, filed on Sep. 16, 1999, now Pat. No. 6,368,328.

(51) Int. Cl.[7] .............................................. A61B 17/24
(52) U.S. Cl. ...................................................... 606/114
(58) Field of Search ............................... 606/110, 113, 606/114, 127, 128, 2.5

(56) References Cited

U.S. PATENT DOCUMENTS

| | | | |
|---|---|---|---|
| 1,054,960 A | | 3/1913 | Butner |
| 3,922,378 A | | 11/1975 | Kline |
| 3,929,138 A | | 12/1975 | Curi |
| 3,996,938 A | | 12/1976 | Clark, III |
| 4,489,722 A | | 12/1984 | Ferraro et al. |
| 4,785,807 A | | 11/1988 | Blanch |
| 4,790,812 A | * | 12/1988 | Hawkins et al. ............... 604/22 |
| 4,816,339 A | | 3/1989 | Tu et al. |
| 4,865,017 A | | 9/1989 | Shinozuka |
| 4,927,426 A | | 5/1990 | Dretler |
| 4,953,548 A | | 9/1990 | Stoddard et al. |
| 5,033,479 A | * | 7/1991 | Tanny ......................... 128/849 |
| 5,040,531 A | * | 8/1991 | Coleman et al. ....... 128/207.14 |
| 5,057,114 A | | 10/1991 | Wittich et al. |
| 5,064,428 A | | 11/1991 | Cope et al. |
| 5,103,816 A | * | 4/1992 | Kirschbaum et al. .. 128/207.14 |
| 5,190,810 A | | 3/1993 | Kirschbaum et al. |
| 5,192,286 A | | 3/1993 | Phan et al. |
| 5,196,228 A | | 3/1993 | Kirby et al. |
| 5,259,570 A | | 11/1993 | Sochard |
| 5,311,863 A | | 5/1994 | Toppses et al. |
| 5,330,482 A | | 7/1994 | Gibbs et al. |
| 5,412,068 A | | 5/1995 | Tang et al. |
| 5,556,426 A | | 9/1996 | Popadiuk et al. |
| 5,558,073 A | | 9/1996 | Pomeranz et al. |
| 5,766,191 A | | 6/1998 | Trerotola |
| 5,788,710 A | | 8/1998 | Bates et al. |
| 5,836,947 A | | 11/1998 | Fleischman et al. |
| 5,860,974 A | | 1/1999 | Abele |
| 5,885,278 A | | 3/1999 | Fleischman |
| 5,904,680 A | | 5/1999 | Kordis et al. |
| 5,935,139 A | | 8/1999 | Bates |
| 5,944,728 A | * | 8/1999 | Bates ......................... 606/127 |
| 5,989,266 A | | 11/1999 | Foster |
| 6,063,082 A | * | 5/2000 | DeVore et al. ................ 606/45 |
| 6,093,195 A | | 7/2000 | Ouchi |
| 6,099,534 A | * | 8/2000 | Bates et al. .................. 606/127 |
| 6,129,739 A | * | 10/2000 | Khosravi ..................... 606/200 |
| 6,174,318 B1 | * | 1/2001 | Bates et al. .................. 606/127 |

FOREIGN PATENT DOCUMENTS

| | | |
|---|---|---|
| WO | 92/16153 | 10/1992 |
| WO | 98/39053 | 9/1998 |
| WO | 99/16363 | 4/1999 |
| WO | 99/16364 | 4/1999 |
| WO | 99/56801 | 11/1999 |

OTHER PUBLICATIONS

Bagley et al., "Laser Division of Intraluminal Sutures," *Journal of Endourology*, vol. 12, No. 4, (1998), pp. 355–357.

* cited by examiner

*Primary Examiner*—Eduardo C. Robert
(74) *Attorney, Agent, or Firm*—Finnegan, Henderson, Farabow, Garrett & Dunner, LLP

(57) ABSTRACT

A medical device used for retrieving material from within a body includes an engaging assembly in which at least a portion of the engaging assembly is resistant to laser energy-induced damage.

23 Claims, 22 Drawing Sheets

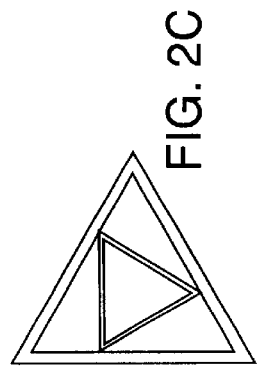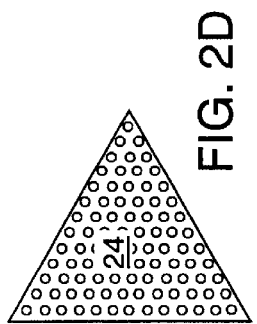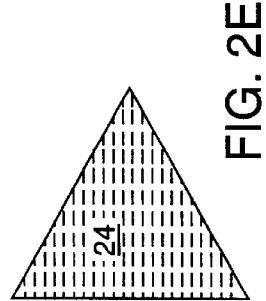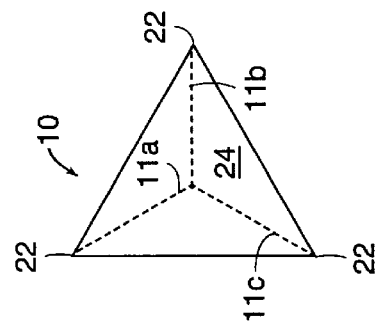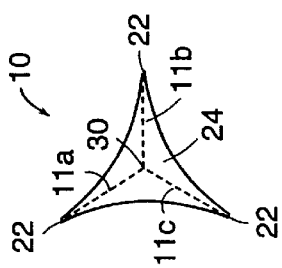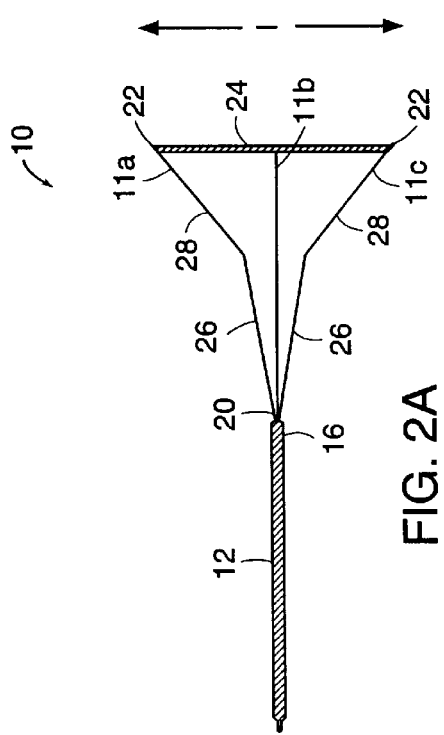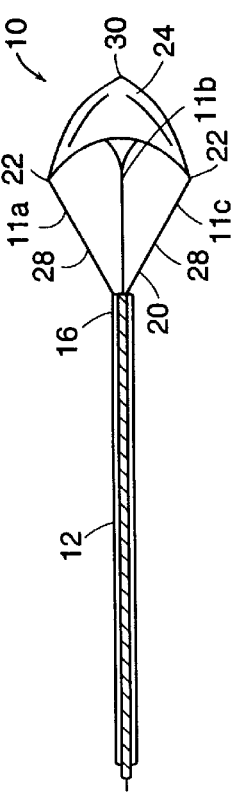

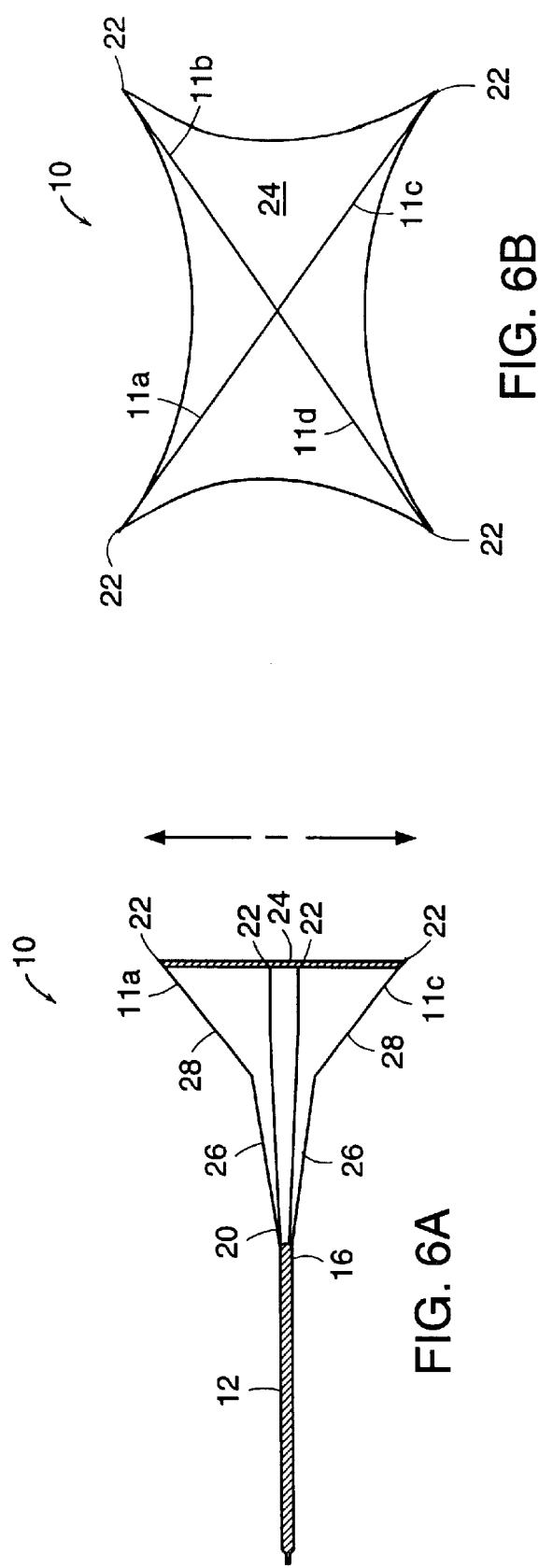
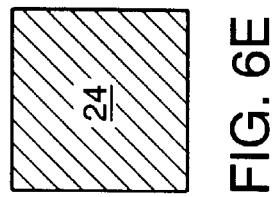
FIG. 6E
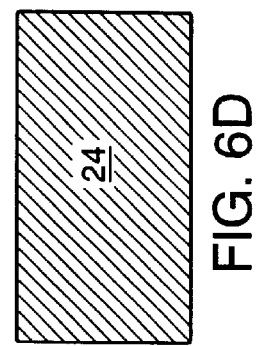
FIG. 6D
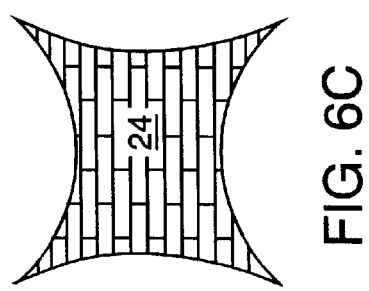
FIG. 6C

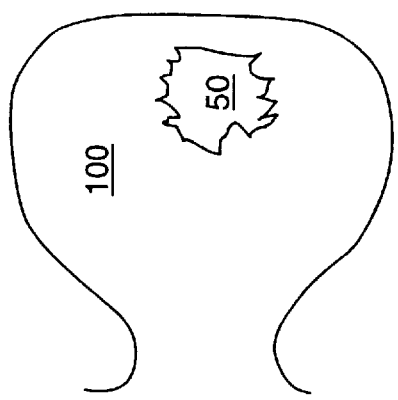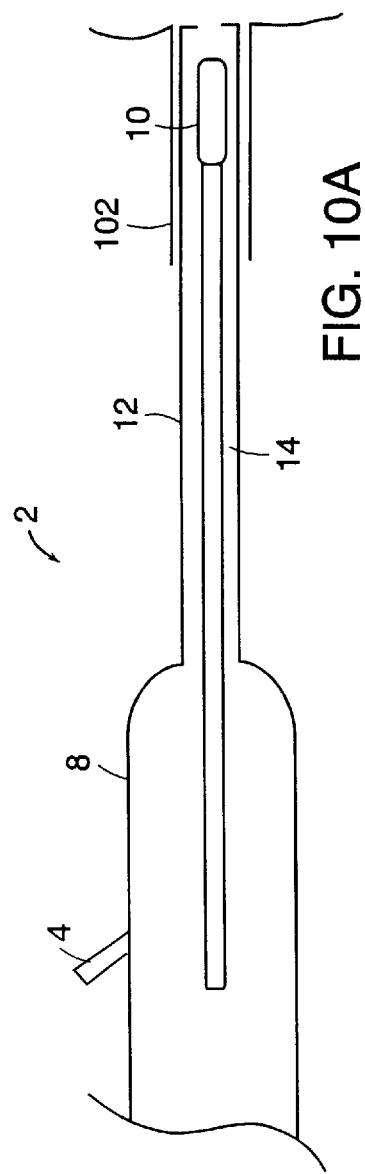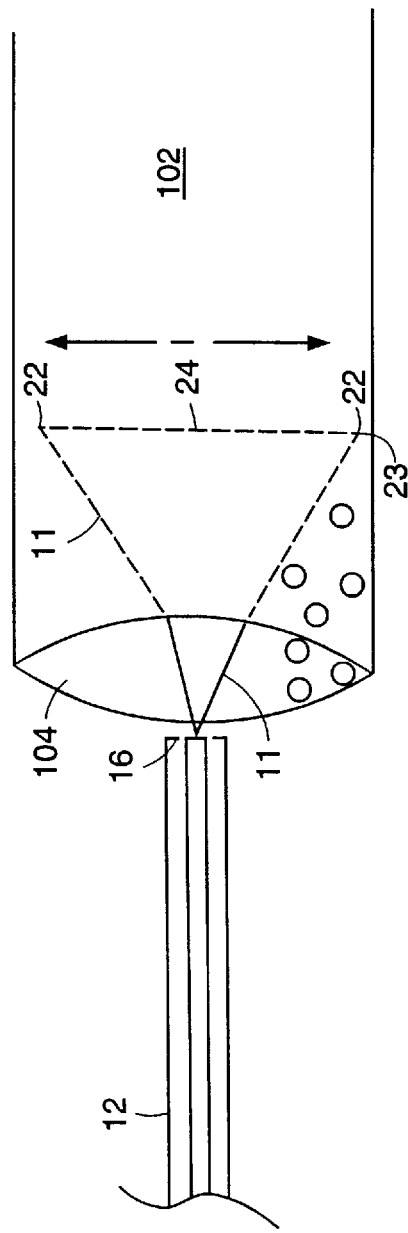

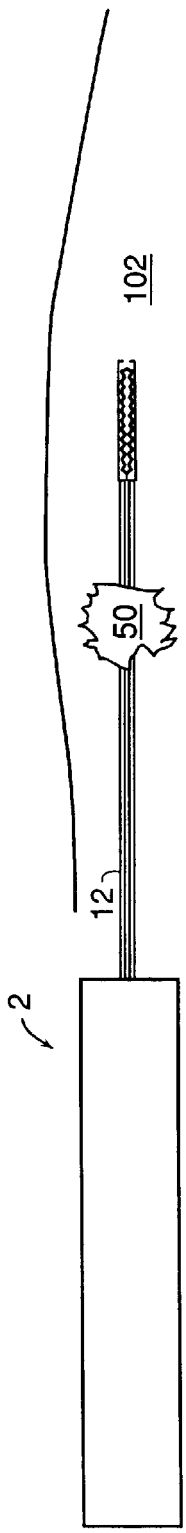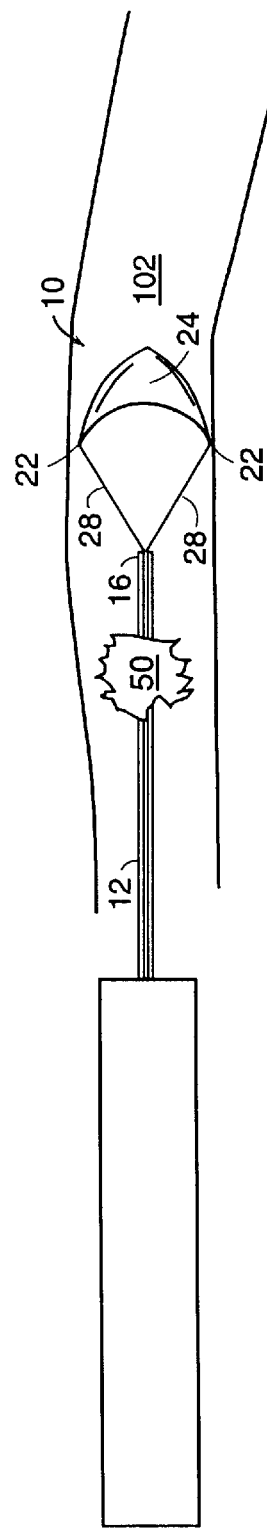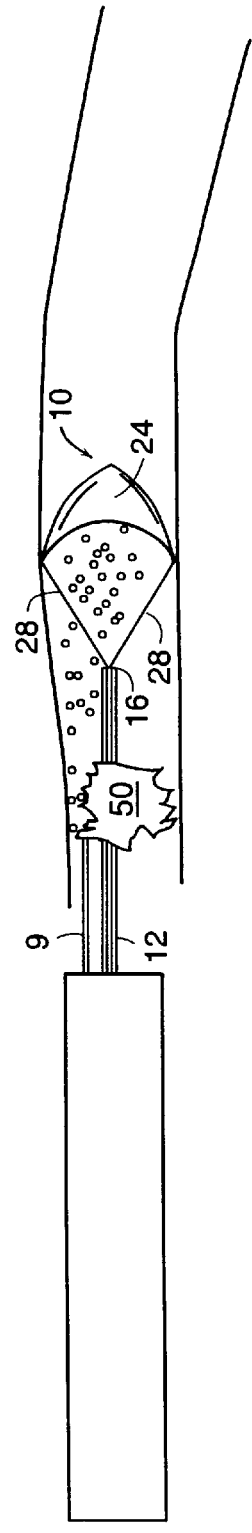

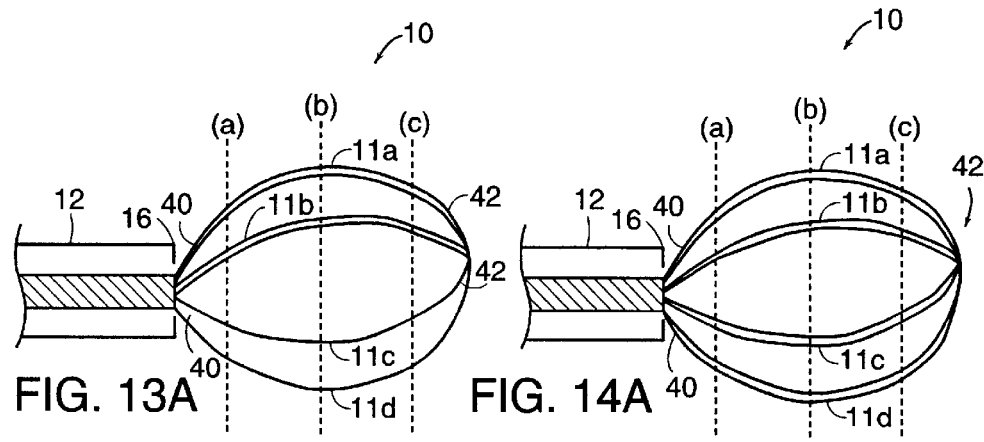
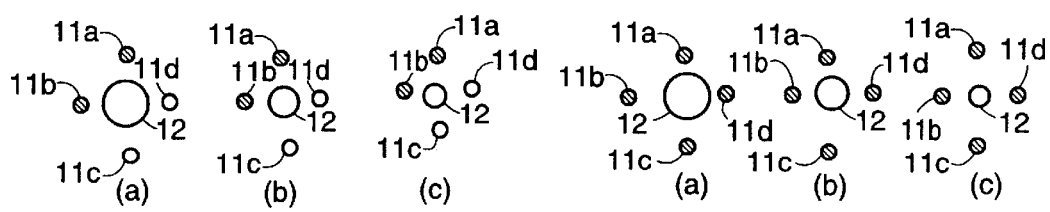
FIG. 13B FIG. 14B
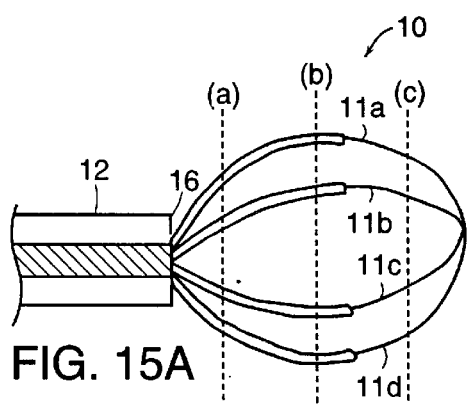
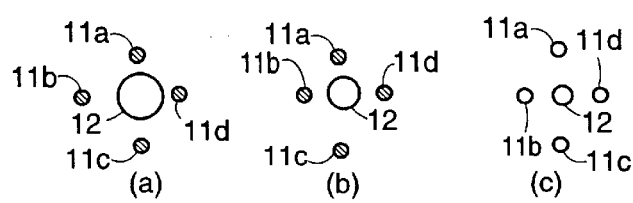
FIG. 15B

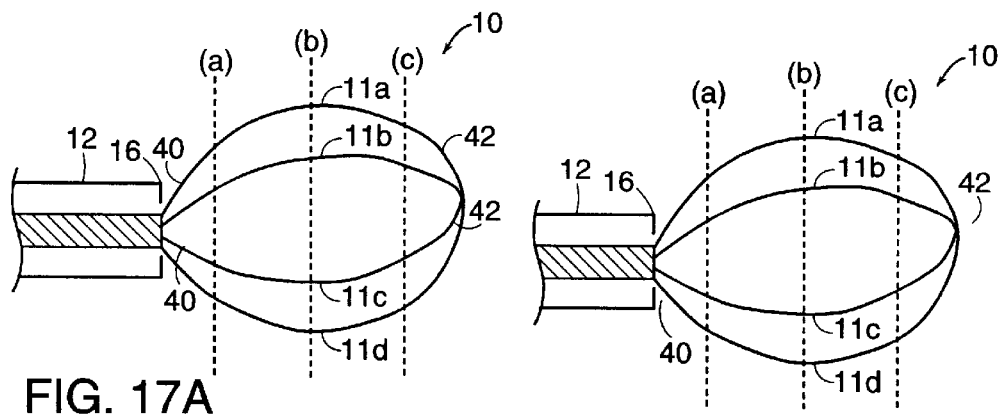
FIG. 17A
FIG. 18A
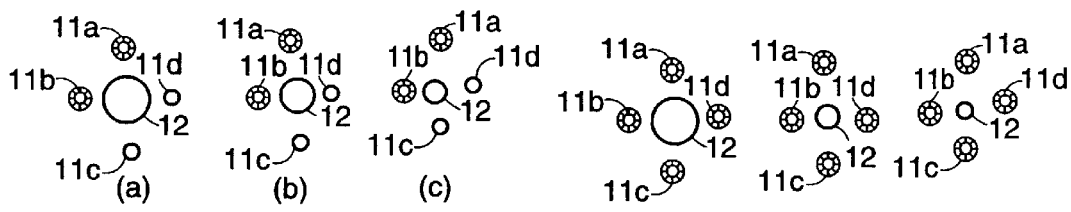
FIG. 17B
FIG. 18B
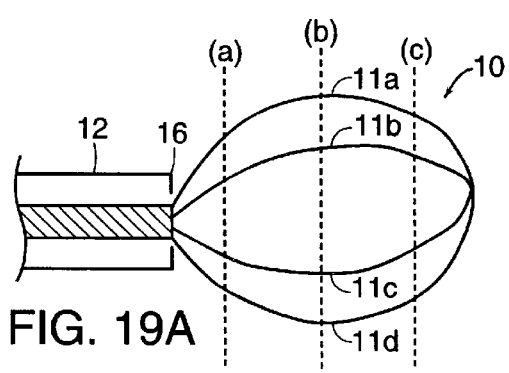
FIG. 19A
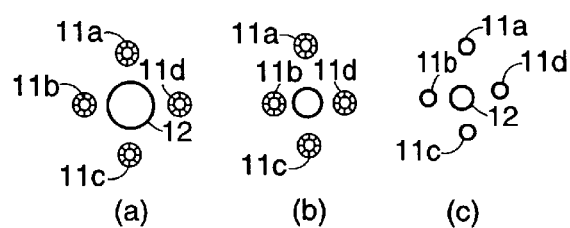
FIG. 19B

LASER-RESISTANT MEDICAL RETRIEVAL DEVICE

This application is a divisional of U.S. Ser.No. 09/398,322, filed Sep. 16, 1999, now U.S. Pat. No. 6,368,328, the disclosure of which is incorporated by reference herein.

TECHNICAL FIELD

This invention relates to medical devices having an engaging assembly for engaging material in a body. More particularly, the invention relates to retrieval assemblies, such as baskets, graspers, forceps, or screens for holding material, such as a stone, in a body tract for treatment of the material by a lithotriptor, e.g., a laser lithotriptor.

BACKGROUND INFORMATION

Medical retrieval devices generally are used to retrieve material, such as a stone, from a body tract or to stabilize material in a body tract for fragmentation by a lithotriptor, such as a laser lithotriptor. In existing medical retrieval devices, the retrieval assembly, such as a basket, is formed from a plurality of wire legs or loops, or by a fabric, such as a metallic fabric or mesh. The retrieval assembly is used to capture material such as a ureteral, urethral, renal, biliary or gallbladder stone. Once the stone is captured in the basket, an attempt is made to remove the stone by withdrawing the medical retrieval device from the body while the stone is captured in the retrieval assembly.

In some clinical situations, a stone located within a body tract is too large or too jagged to be withdrawn from the body tract while captured in the retrieval assembly of a medical retrieval device. Under these conditions, the stone must be fragmented into smaller particles.

When stones are fragmented within a body tract by a lithotriptor, the stone must first be stabilized. Typically, a medical retrieval device is used to capture a stone in the retrieval assembly. With the stone held in position within the retrieval assembly, a lithotriptor, such as a laser lithotriptor, comes into proximity with the stone and the stone is fragmented by the lithotriptor. After the stone is fragmented, the stone fragments can be removed by the same or a different medical retrieval device, or the fragments can be left in the body to be eliminated naturally.

Laser lithotriptors have gained increasingly wide application in the treatment of stones that are lodged within a body tract. Several lasers, such as the Nd: YAG laser and the holmium: YAG laser, have become available for medical applications.

SUMMARY OF THE INVENTION

In general, the invention relates to a medical retrieval device comprising a handle, a sheath having a lumen, and a laser-resistant engaging assembly for retrieving material from a body. At least a portion of the laser-resistant engaging assembly includes at least one substance that is resistant to damage induced by laser energy. The laser-resistant substance can be incorporated within the engaging assembly itself or coated on the engaging assembly. The laser-resistant substance can be a fluorocarbon plastic such as expanded polytetrafluoroethylene (EPTFE), polytetrafluoroethylene (PTFE), tetrafluoroethylene (TFE), fluorinated ethylenepropylene (FEP), perfluoroalkoy (PFA), ethylene tetrafluoroethylene (ETFE), polyvinylidene fluoride (PVDF). The laser resistant material can also be ceramics or gold, silver or nickel plating polished to a reflective surface, or any material (or combination of materials) that is resistant to damage induced by laser energy released from medical lasers, such as, medical Nd: YAG or holmium: YAG lasers.

Medical retrieval devices having engaging assemblies that are resistant to laser energy in accordance with the invention have advantages over conventional medical retrieval devices when the inventive devices are used in combination with laser energy therapy. For example, laser lithotriptors are effective in fragmenting stones that are captured in a retrieval assembly of a medical retrieval device. One drawback of the combined use of a laser lithotriptor and retrieval assembly is the susceptibility of the retrieval assembly, or parts of the retrieval assembly, to laser energy-induced damage. Damage may be caused by misfiring, misdirection or unavoidable misalignment of the laser lithotriptor with the stone. Laser energy-induced retrieval assembly damage may cause components of the retrieval assembly, such as the legs, to become roughened or broken. Broken or roughened legs expose sharp ends or surfaces that can traumatize the body tract.

An advantage of a medical retrieval device according to the invention is that its engaging assembly is resistant to damage from incident laser energy. Any damage to the engaging assembly caused by laser energy could potentially traumatize the body tract into which the medical device is placed. By including laser-resistant materials in at least a portion of the engaging assembly, the risk of trauma to a body tract that could be induced by a damaged engaging assembly is reduced or eliminated.

In one aspect, the invention features a medical retrieval device comprising a handle, a sheath having a lumen, and a laser-resistant engaging assembly for engaging material in a body. The laser-resistant engaging assembly includes a substance resistant to damage induced by laser energy. The laser-resistant substance is incorporated into at least a portion of the components of the engaging assembly or applied to at least a portion of the surface of the engaging assembly. The laser-resistant engaging assembly has a position in which the laser-resistant engaging assembly is enclosed within the lumen of the sheath (a closed position) and another position in which the laser-resistant engaging assembly extends from the distal end of the sheath and out of the sheath lumen (an open position). The laser-resistant engaging assembly can transition between the closed position and the open position by axial movement of the sheath over the engaging assembly, or the engaging assembly can move axially as the sheath stays fixed. In general, there can be relative movement between the sheath and the engaging assembly to place the engaging assembly in the closed position, the open position, or any position between the closed and open positions.

An embodiment in accordance with this aspect of the invention can include an elongated member that extends axially in the sheath lumen, is operably attached at its distal end to the laser-resistant engaging assembly, and is joined at its proximal end to an actuator in the handle. In this embodiment, the laser-resistant engaging assembly is moved when the elongated member is moved by the actuator in the handle.

Other embodiments in accordance with this aspect of the invention can include a laser-resistant engaging assembly such as a surgical retrieval basket comprising a plurality of legs, or, alternatively, a plurality of loops. The laser-resistant engaging assembly can also have a single loop configuration. In some embodiments, the laser-resistant medical retrieval basket has a tipless, or atraumatic tip, at the distal end of the basket. In still other embodiments, the laser-resistant basket can have at least one individually-actuateable leg, or a D-shaped, V-shaped or rectangular leg. The inside surface or the outside surface of at least one leg can be treated with at least one laser-resistant substance.

In another embodiment, the laser-resistant engaging assembly has a proximal portion and a distal portion. A distal portion of the laser-resistant engaging assembly can be used for capturing material in a body when the distal portion is extended beyond the distal end of the sheath and a proximal portion of the assembly is collapsed within the sheath. With this embodiment of the laser-resistant engaging assembly, the captured material can be released from the engaging assembly when the distal and proximal portions of the engaging assembly extend beyond the distal end of the sheath.

In yet another embodiment of the invention, the laser-resistant engaging assembly includes a grasper having a plurality of opposing loops, such as two loops, the loops being attached at the base of the engaging assembly and unattached to one another at their distal ends. The loops of the laser-resistant retrieval assembly have a collapsed position in which the loops are collapsed within the lumen of the sheath, and another position in which at least a portion of the loops extend from the distal end of the sheath and out of the lumen. The loops are moveable between an open and a closed position with the distal ends of the loops being closer together in the closed position than when in the open position to allow capture and release of material.

In another aspect, the invention involves a method for treating material in a body. The method includes the steps of inserting a medical retrieval device into a body having a proximal handle, a sheath having a lumen and an engaging assembly. The engaging assembly has at least a position in which the engaging assembly is within the lumen of the sheath and another position in which the engaging assembly extends from a distal end of the sheath and out of the sheath lumen. At least a portion of the engaging assembly includes a substance resistant to damage from laser energy. The material in the body is held by the engaging assembly and is treated by the laser. The medical device is removed from the body.

BRIEF DESCRIPTION OF THE DRAWINGS

In the drawings, like reference characters generally refer to the same parts throughout the different views. Also, the drawings are not necessarily to scale, emphasis instead generally being place upon illustrating the principles of the invention.

FIG. 2A illustrates a side-view of an embodiment of a three-wire laser-resistant fabric retrieval assembly in a fully deployed position.

FIG. 2B illustrates an end-view of the laser-resistant fabric retrieval assembly illustrated in FIG. 2A in a fully deployed position.

FIG. 2C illustrates an end-view of another embodiment of the three-wire laser-resistant fabric retrieval assembly illustrated in FIG. 2A.

FIG. 2D illustrates an end-view of another embodiment of the three-wire laser-resistant fabric retrieval assembly illustrated in FIG. 2A.

FIG. 2E illustrates an end-view of another embodiment of the three-wire laser-resistant fabric retrieval assembly illustrated in FIG. 2A.

FIG. 3A illustrates a side-view of an embodiment of a three-wire laser-resistant fabric retrieval assembly in a partially deployed, convex configuration.

FIG. 3B illustrates an end-view of the laser-resistant fabric retrieval assembly illustrated in FIG. 3A in a partially deployed, convex configuration.

FIG. 6A illustrates a side-view of an embodiment of a four-wire laser-resistant fabric retrieval assembly in a fully deployed position.

FIG. 6B illustrates an end-view of the laser-resistant fabric retrieval assembly illustrated in FIG. 6A in a fully deployed position according to the invention.

FIG. 6C illustrates an end-view of another embodiment of the four-wire laser-resistant fabric retrieval assembly illustrated in FIG. 6A.

FIG. 6D illustrates an end-view of another embodiment of the four-wire laser-resistant fabric retrieval assembly illustrated in FIG. 6A.

FIG. 6E illustrates an end-view of another embodiment of the four-wire laser-resistant fabric retrieval assembly illustrated in FIG. 6A.

FIG. 10A illustrates a diagrammatic representation of a medical retrieval device according to the invention entering a body tract to retrieve a renal stone.

FIG. 10E illustrates a diagrammatic representation of the retrieval device in FIG. 10D with the retrieval assembly positioned to scrape stone fragments towards a body orifice.

FIG. 11C illustrates a diagrammatic representation of a medical retrieval device, according to the invention, with the retrieval assembly collapsed in the lumen of a ureter.

FIG. 11D illustrates a diagrammatic representation of the medical retrieval device according to the invention illustrated in FIG. 11C with the retrieval assembly positioned distal to the stone and partially deployed.

FIG. 11E illustrates a diagrammatic representation of the medical retrieval device according to the invention as illustrated in FIG. 11C, a lithotriptor and a stone fragmented by the lithotriptor.

FIG. 13A illustrates an embodiment of a retrieval assembly according to the invention having two legs including at least one substance resistant to laser energy-induced damage.

FIG. 13B illustrates a cross-section of the retrieval assembly in FIG. 13A.

FIG. 14A illustrates an embodiment of a retrieval assembly according to the invention with four legs including at least one substance resistant to laser energy-induced damage.

FIG. 14B illustrates a cross-section of the retrieval assembly in FIG. 14A.

FIG. 15A illustrates an embodiment of a retrieval assembly according to the invention with a portion of each of four legs including at least one substance resistant to laser energy-induced damage.

FIG. 15B illustrates a cross-section of the retrieval assembly in FIG. 15A.

FIG. 17A illustrates an embodiment of a retrieval assembly according to the invention with two legs coated with at least one substance that is resistant to laser energy-induced damage.

FIG. 17B illustrates a cross-section of the retrieval assembly illustrated in FIG. 17A.

FIG. 18A illustrates an embodiment of a retrieval assembly according to the invention with four legs coated with at least one substance resistant to laser energy-induced damage.

FIG. 18B illustrates a cross-section of the retrieval assembly illustrated in FIG. 18A.

FIG. 19A illustrates an embodiment of a retrieval assembly according to the invention with a portion of each of four legs coated with at least one substance that is resistant to laser energy-induced damage.

FIG. 19B illustrates a cross-section of the retrieval assembly illustrated in FIG. 19A.

DESCRIPTION

All of the following embodiments of the invention generally have at least one thing in common, and that is that all or a portion of an engaging assembly, retrieval assembly, or gripping assembly of a medical retrieval device is resistant to laser energy-induced damage.

Figure 1A:
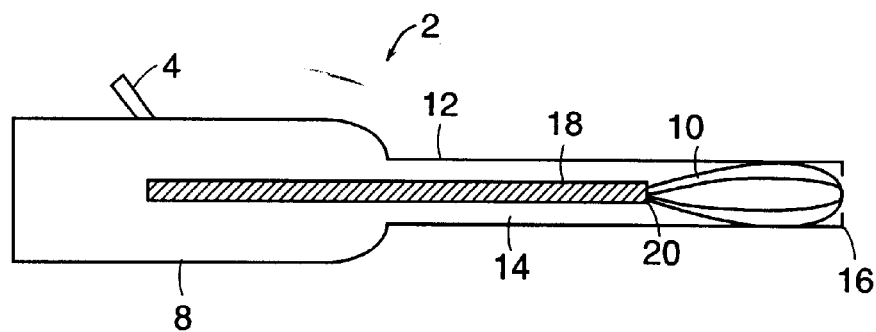
FIG. 1A illustrates a plan view of a medical retrieval device according to the invention with a handle at a proximal end and a laser-resistant retrieval assembly opposite the handle enclosed within a sheath.
Figure 1B:
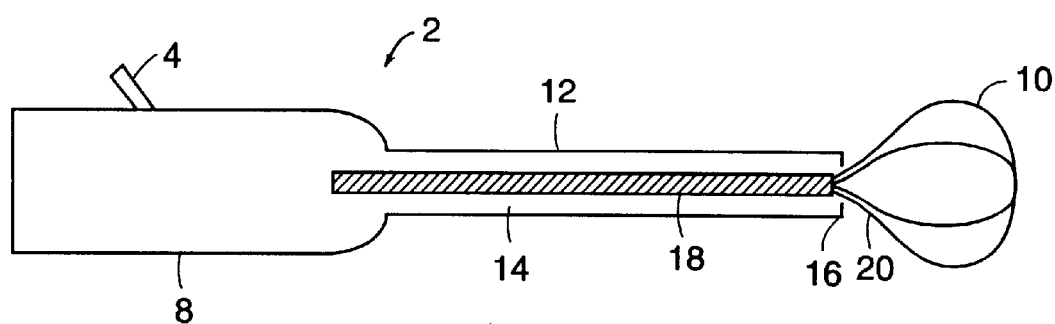
FIG. 1B illustrates a plan view of the medical retrieval device according to the invention illustrated in FIG. 1A with the laser-resistant retrieval assembly opposite the handle extended from the distal end of the sheath.

In one aspect of the invention, referring generally to FIG. 1A, a medical retrieval device 2 of the invention includes a laser-resistant retrieval assembly 10, for example, a laser-resistant basket 10. The laser-resistant basket 10 is the type that can be collapsed within a sheath 12 for entry into the body and can be constructed with basket legs, loops or fabrics. A medical retrieval device 2 that includes the laser-resistant basket 10 and sheath 12 also includes a proximal handle 8. The handle 8, sheath 12, and laser-resistant basket 10 illustrated in FIGS. 1A and 1B are not shown in their correct size or proportion to each other. The size of the entire device is dimensioned to fit the requirements of its application in the body. For example, for urological applications, the size of the portion of the device inserted into a body tract is typically 1.7–8.0 Fr. The sheath 12 has at least one lumen 14 therein and extends from the handle 8 to a distal end 16 of the sheath. At least one elongated member such as a cable, coil, shaft, guidewire or mandril wire 18 extends within the lumen 14 from an actuating mechanism 4 at the device handle 8, to the base 20 of the laser-resistant basket 10. The one or more actuating mechanisms 4 is operably attached to the basket 10, and is operated by an operator to cause the basket 10 to move in and out of the sheath 12, between a collapsed/retracted position within the sheath 12 as illustrated in FIG. 1A, to an extended position outside of the sheath 12, where the laser-resistant basket 10 is open/expanded and extending beyond the distal end of the sheath 16, as shown in FIG. 1B. Alternatively, the actuating mechanism 4 causes the sheath 12 to advance in a distal direction over the stationary laser-resistant basket 10 and cable 18 combination, to thereby collapse the laser-resistant basket 10 within the sheath 12, and the actuating mechanism 4 slides the moveable sheath 12 in a proximal direction to expose the stationary laser-resistant basket 10 and allow the basket to open/ expand.

Figure 1C:
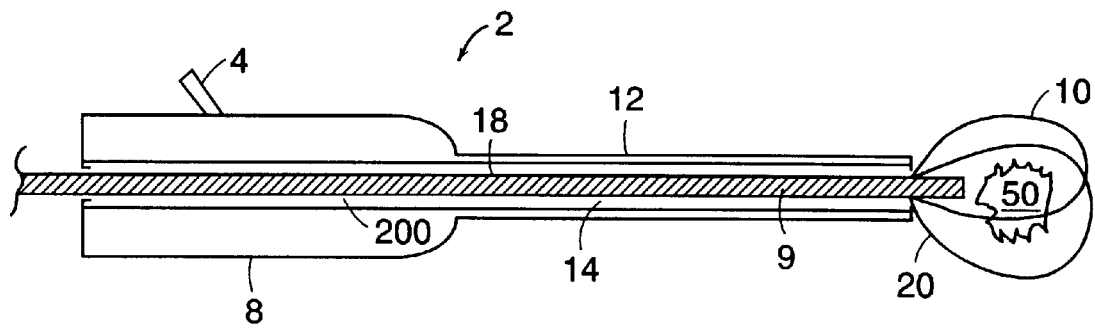
FIG. 1C illustrates a plan view of the medical retrieval device according to the invention illustrated in FIG. 1A with a stone captured in the interior of the laser-resistant retrieval assembly and a lithotriptor extended through a channel of the medical retrieval device.

Referring to FIG. 1C, in another embodiment of the medical retrieval device according to the invention, a lithotriptor device 9, such as a laser lithotriptor, extends longitudinally through a channel 200 in the handle 8 and sheath 12, into the lumen at the basket base 20 of the laser-resistant basket 10. Such laser lithotriptor devices are used to fragment stones 50 that have been engaged in the laser resistant basket 10.

In general, both types of laser-resistant basket/sheath movement configurations and related handle mechanisms, and many types of laser lithotriptor devices are known, and can be seen in existing product designs available from, for example, Boston Scientific Corporation (Natick, Mass.).

Figure 1D:
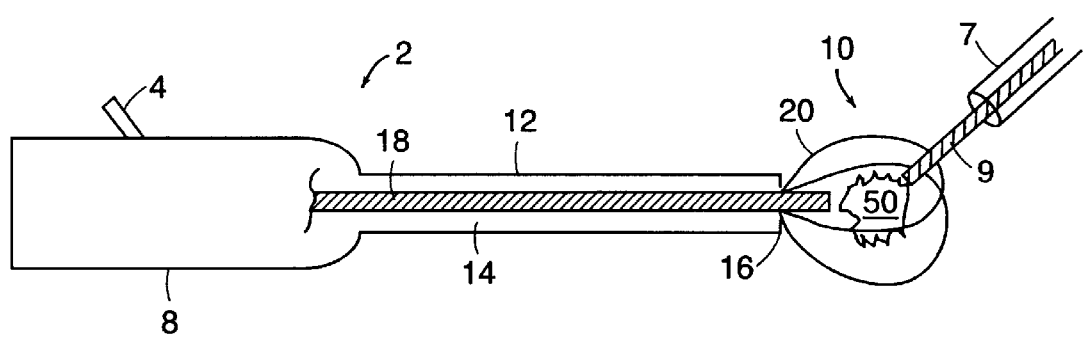
FIG. 1D illustrates a plan view of a medical retrieval device according to the invention illustrated in FIG. 1A with a stone captured in the interior of the retrieval assembly and a lithotriptor in a second endoscopic device approaching the stone.

With the laser-resistant basket collapsed within the sheath 12 as shown in FIG. 1A, the sheath 12 can be inserted into the body by an operator to a site in the body where the material to be retrieved is located (e.g., a stone in the ureter). By next placing the laser-resistant basket 10 into its open/ expanded position, i.e., fully deployed as illustrated in FIG. 1B, the laser-resistant basket 10 dilates the body tract in which it has been placed and can be manipulated by the operator to engage material by gripping, grasping, entrapping, capturing, or by supporting the material within the laser-resistant basket 10. A laser lithotriptor can pass through the medical retrieval device 2 into the lumen of the laser-resistant basket 10 as shown in FIG. 1C. As shown in FIG. 1D, alternatively, a laser lithotriptor 9 can be introduced into the laser-resistant basket 10 adjacent the stone 50 to fragment the captured stone 50 by alternate means 7 that are independent of the medical retrieval device. Laser energy can be applied to the stone 50, fragmenting it. The stone fragments are removed in the laser resistant basket when it is withdrawn from the body or, if the fragments are small enough, the fragments are left within the body to be eliminated naturally.

In one embodiment of this aspect of the invention, referring to FIG. 2A and FIG. 2B, the laser-resistant retrieval assembly 10 of the medical retrieval device has three resilient legs 11a, 11b, and 11c. As illustrated in FIGS. 2A and 2B, the laser-resistant retrieval assembly 10 is fully deployed from the distal end 16 of the sheath 12. The retrieval assembly is moved relative to the sheath by moving the sheath over the stationary retrieval assembly or by moving the retrieval assembly in and out of a stationary sheath, as discussed above. The proximal end 20 of each of the three legs 11a, 11b, 11c is joined to elongated member 18, and the distal end 22 of each of the three legs 11a, 11b, 11c is secured to a laser-resistant fabric 24. The fabric can be secured by any means known in the art, for example, by making a hole in the fabric, threading a leg through the hole, bending the leg onto itself and soldering the leg to itself.

The fabric 24 illustrated in FIGS. 2A–2E is laser-resistant. Laser-resistant materials that may be used to manufacture the fabric include fluorocarbon plastics such as expanded polytetrafluoroethylene (EPTFE), polytetrafluoroethylene (PTFE) tetrafluoroethylene (TFE), fluorinated ethylenepropylene (FEP), perfluoroalkoy (PFA), ethylene tetrafluoroethylene (ETFE), polyvinylidene fluoride (PVDF). The laser resistant material can also be ceramics or gold, silver or nickel plating polished to a reflective surface. The laser resistant fabric can be made from a mesh material. The mesh can have openings with a diameter of 3.0 mm or less to allow small stones to pass through and to retain larger stones. Mesh openings less than 3.0 mm are preferred to entrap small stones and maximize lesser energy shielding. As illustrated in FIGS. 2B–2E, the laser-resistant fabric 24 is triangular-shaped. The triangular shape illustrated is not intended to be limiting. With the three-legged retrieval assembly, other fabric shapes are possible, such as rectangular, oval, semi-circular or circular. The texture of laser-resistant fabric 24 includes, but is not limited to, a mesh or net. For example, the laser resistant fabric 24 can be a solid, non-woven sheet of material. Openings in the fabric can be cut out or stamped out.

The legs of the laser-resistant fabric retrieval assembly are manufactured from shape memory materials, stainless steel, polymers, or other materials known to be used in medical retrieval devices.

Referring to FIG. 2A, the resilient legs 11a, 11b, 11c of the laser-resistant retrieval assembly 10 have two portions, a proximal portion 26 and a distal portion 28. The distal portion 28 of each leg 11 is bent outward from the central long axis of the laser-resistant retrieval assembly 10 at an angle of approximately 45 degrees. The range of possible angles is 0° to 90°, preferably 35° to 60°. Thus, when the laser-resistant retrieval assembly 10 is fully deployed by extending the proximal portion 26 and distal portion 28 of the legs beyond the distal end 16 of the sheath 12, the distal ends 22 of the legs 11 are maximally parted at distance "1" from the distal end 22 of the other legs 11 of the retrieval assembly 10, as illustrated in FIG. 2A. The laser-resistant fabric 24, secured to the distal ends 22 of the three legs 11a, 11b, 11c of the laser-resistant retrieval assembly 10, forms a taut, flat surface as illustrated from the side in FIG. 2A and from the end of the laser-resistant retrieval assembly 10 in FIGS. 2B–2E. The taut, flat surface of the three-leg laser-resistant fabric 24 can serve as a screen or backstop for a stone while the stone is being fragmented by a laser lithotriptor, for example. Alternatively, the fabric 24 in its flat, taut configuration, can be used as a scraper to reposition stones in or remove stones from the body.

In another embodiment of the invention, referring to FIGS. 3A and 3B, when the three-leg laser-resistant retrieval assembly 10 is only partially deployed from the distal end 16 of the sheath 12, the laser-resistant retrieval assembly 10 can assume a convex shape. As illustrated from the side in FIG. 3A, and from the end of the laser-resistant retrieval assembly in FIG. 3B, when the distal portion 28 of the resilient legs of the laser-resistant retrieval assembly 10 are extended beyond the distal end 16 of the sheath 12, and the proximal portion 26 of the legs remain enclosed within the sheath 12, the laser-resistant fabric 24 secured to the distal end 22 of the legs is everted to a convex shape; the apex 30 of the convex shape is positioned further from the distal end 16 of the sheath 12 than are the distal ends 22 of the legs of the laser-resistant retrieval assembly 10. Thus, the three-leg laser-resistant retrieval assembly 10 takes on an umbrella-shape as shown in FIG. 3A.

Figure 4B:
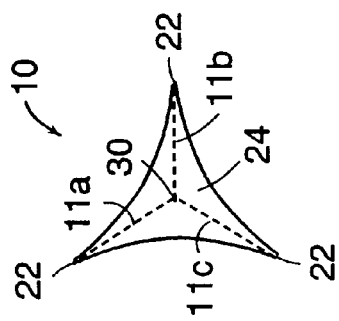
FIG. 4B illustrates an end-view of the laser-resistant fabric retrieval assembly illustrated in FIG. 4A in a partially deployed, concave configuration.
Figure 4A:
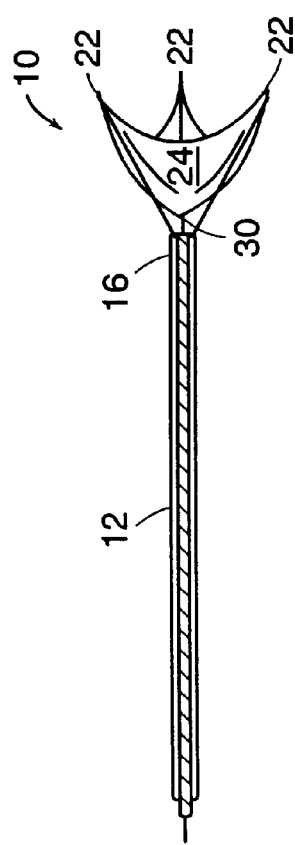
FIG. 4A illustrates a side-view of an embodiment of a three-wire laser-resistant fabric retrieval assembly in a partially deployed, concave, grasper or forceps-like configuration.

In an alternate configuration of this embodiment of the laser-resistant retrieval assembly, referring to the side view of the retrieval assembly 10 illustrated in FIG. 4A and the end-view of the laser-resistant retrieval assembly 10 illustrated in FIG. 4B, when the distal portion 28 of the legs 11 of the laser-resistant retrieval assembly 10 are extended beyond the distal end 16 of the sheath 12, and the proximal portion 26 of the legs 11 remain enclosed by the sheath 12, the laser-resistant fabric 24 secured to the distal end 22 of the legs 11 of the laser-resistant retrieval assembly 10, can be inverted to a concave shape, or grasping, or forceps-like retrieval assembly; the apex 30 of the concave shape is positioned more closely to the distal end 16 of the sheath than are the distal ends 22 of the laser-resistant retrieval assembly legs 11. Thus, the three-leg laser-resistant retrieval assembly 10 takes on a grasping or forceps-like configuration.

Figure 5B:
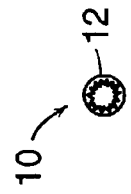
FIG. 5B illustrates an end-view of the laser-resistant fabric retrieval assembly illustrated in FIG. 5A collapsed within the sheath according to the invention.
Figure 5A:
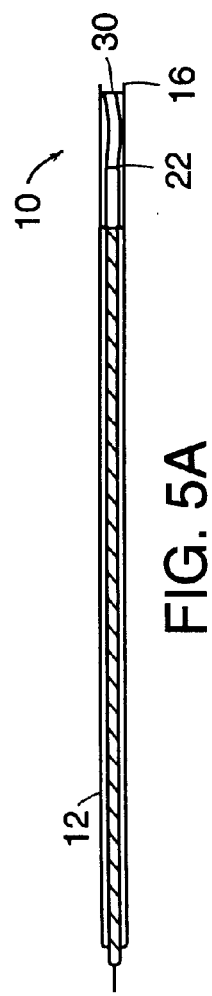
FIG. 5A illustrates a side-view of an embodiment of a three-wire laser-resistant fabric retrieval assembly collapsed within the sheath according to the invention.

The three-leg laser-resistant retrieval assembly 10 can be completely enclosed within the sheath of the medical retrieval device. Referring to the side view of the three-leg laser-resistant retrieval assembly 10 shown in FIG. 5A and the end-view of the retrieval assembly 10 shown in FIG. 5B, the laser-resistant retrieval assembly is enclosed within the sheath 12 when the proximal portion 26 and the distal portion 28 of the laser-resistant retrieval assembly legs are withdrawn through the distal end 16 of the sheath into the lumen 14 of the sheath 12. In this configuration, the medical retrieval device can be easily inserted into the body tract of a patient.

Referring now to FIG. 6A and FIG. 6B, in another embodiment of this aspect of the invention, the laser-resistant retrieval assembly 10 of the medical retrieval device has four legs 11a, 11b, 11c and 11d. With the laser-resistant retrieval assembly fully deployed from the distal end 16 of the sheath 12, as illustrated in FIGS. 6A and 6B, the proximal end 20 of each of the four legs is joined to elongated member 18 and the distal end 22 of each of the four legs is secured to laser-resistant fabric 24.

The laser-resistant fabric 24 of a four-leg retrieval assembly, illustrated in FIGS. 6B–6E, is manufactured from the same material as the laser-resistant fabric 24 of the three-leg laser-resistant retrieval assembly described above. As illustrated in FIGS. 6B–6E, the laser-resistant fabric 24 is generally rectangular in shape. The rectangular shapes illustrated in FIGS. 6B–6E are not intended to be limiting to just the shapes illustrated. Other shapes of the laser-resistant fabric are also possible, such as square, oval, semi-circular, or circular. The texture of the laser-resistant fabric 24 includes, but is not limited to, a mesh or net.

Referring to FIG. 6A, the legs 11a, 11b, 11c, 11d of the laser-resistant retrieval assembly 10 each have two portions, a proximal portion 26 and a distal portion 28. The distal portion 28 of each leg is bent outward from the central long axis of the laser-resistant retrieval assembly at an angle of approximately 45 degrees. The range of possible angles is 0° to 90°, preferably 35° to 60° Thus, when the laser-resistant retrieval assembly 10 is fully deployed by extending the proximal portion 26 and distal portion 28 of the legs beyond the distal end 16 of the sheath 12, the distal ends 22 of the legs 11 of the retrieval assembly 10 are maximally parted at distance "1" from the distal ends 22 of the other legs 11 as illustrated in FIG. 6A. The laser-resistant fabric 24, secured to the distal ends 22 of the four legs 11a, 11b, 11c, 11d of the laser-resistant retrieval assembly 10, forms a taut, flat surface as illustrated from the side of the laser-resistant retrieval assembly 10 shown in FIG. 6A and from the end of the laser-resistant retrieval assembly 10 shown in FIGS. 6B–6E. The taut, flat surface of the four-leg laser-resistant fabric 24 can serve as a screen or backstop for a stone while the stone is being fragmented by a laser lithotriptor, for example. Alternatively, the fabric 24 in its flat, taut configuration, can be used as a scraper to reposition stones in the body.

Figure 7B:
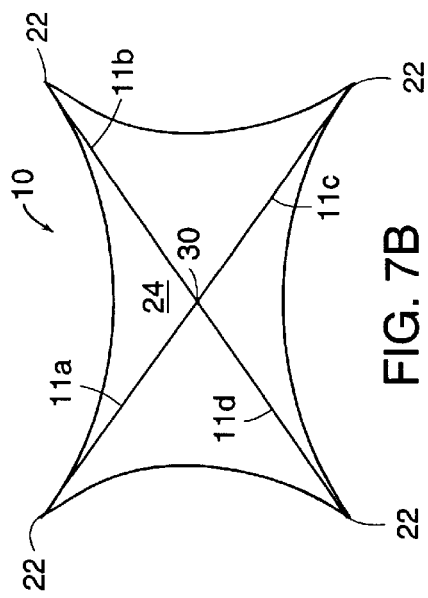
FIG. 7B illustrates an end-view of the laser-resistant fabric retrieval assembly illustrated in FIG. 7A in a partially deployed, convex configuration.
Figure 7A:
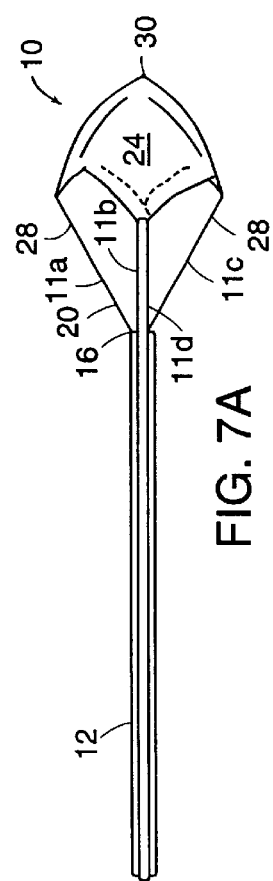
FIG. 7A illustrates a side-view of a four-wire laser-resistant fabric retrieval assembly in a partially deployed, convex configuration.

In another embodiment, referring to FIGS. 7A and 7B, when the four-leg laser-resistant retrieval assembly 10 is only partially deployed from the distal end of the sheath 12, the laser-resistant retrieval assembly 10 can assume a convex shape. As illustrated from the side of the laser-resistant retrieval assembly in FIG. 7A and from the end of the laser-resistant retrieval assembly in FIG. 7B, when only the distal portion 28 of the legs of the laser-resistant retrieval assembly 10 are extended beyond the distal end 16 of the sheath 12, and the proximal portion 26 of the legs 11 remain enclosed by the sheath 12, the laser-resistant fabric 24 secured to the distal end 22 of the legs is everted to a convex shape; the apex 30 of the convex shape is positioned further from the distal end 16 of the sheath 12 than the distal ends 22 of the legs 11 of the laser-resistant retrieval assembly 10. Thus, the four-leg laser-resistant retrieval assembly 10 takes on an umbrella-shape.

Figure 8B:
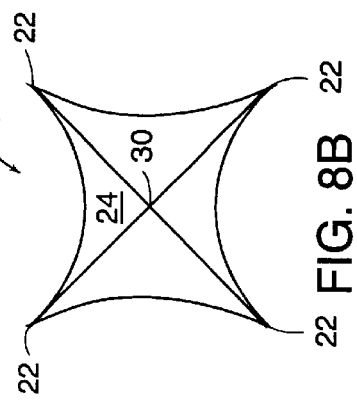
FIG. 8B illustrates an end-view of the laser-resistant fabric retrieval assembly illustrated in FIG. 8A in a partially deployed, concave configuration.
Figure 8A:
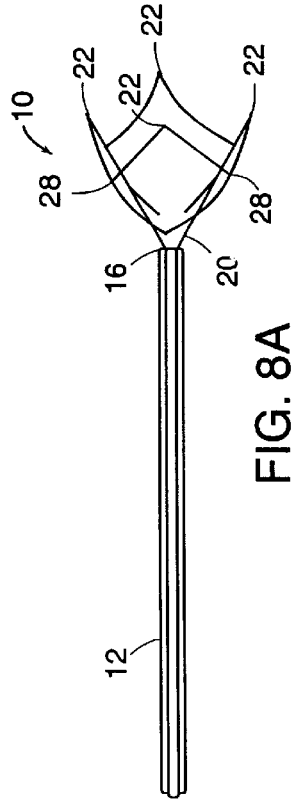
FIG. 8A illustrates a side-view of a four-wire laser-resistant fabric retrieval assembly in a partially deployed, concave, grasper or forceps-like configuration.

In an alternate configuration of this embodiment of the laser-resistant retrieval assembly, referring to the side view of the laser-resistant the retrieval assembly 10 in FIG. 8A and the end view of the laser-resistant retrieval assembly 10 illustrated in FIG. 8B, when only the distal portion 28 of the legs 11 of the laser-resistant retrieval assembly 10 are extended beyond the distal end 16 of the sheath 12, and the proximal portion 26 of the legs 11 remain enclosed by the sheath 12, the laser-resistant fabric 24 secured to the distal end 22 of the legs 11 of the laser-resistant retrieval assembly 10, can be inverted to a concave shape, or grasper, or forceps-like retrieval assembly; the apex 30 of the concave shape is positioned more closely to the distal end 16 of the sheath than the distal ends 22 of the retrieval assembly legs 11. Thus, the four-leg laser-resistant retrieval assembly 10 takes on a grasper or forceps-like configuration.

Figure 9B:
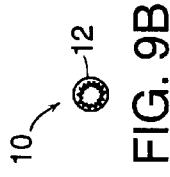
FIG. 9B illustrates an end-view of the laser-resistant fabric retrieval assembly illustrated in FIG. 9A collapsed within the sheath according to the invention.
Figure 9A:
FIG. 9A illustrates a side-view of a four-wire laser-resistant fabric retrieval assembly collapsed within the sheath according to the invention.

The four-leg retrieval assembly 10 can be completely enclosed within the sheath 12 of the medical retrieval device 2. Referring to the side-view of the four-leg laser-resistant retrieval assembly 10 shown in FIG. 9A and the end-view of the four-leg laser-resistant retrieval assembly 10 shown in FIG. 9B, the laser-resistant retrieval assembly 10 is enclosed within the sheath 12 when the proximal portion 26 and the distal portion 28 of the basket legs 11 are withdrawn into the lumen 14 of the sheath 12 through the distal end 16 of the sheath 12. In this configuration, the medical retrieval device 2, including a four leg laser-resistant retrieval assembly 10, can be inserted into the body tract of a patient.

According to the invention, the medical retrieval device including a laser-resistant fabric retrieval assembly may have more than the three or four legs illustrated, such as 5, 6, 8 or 10 legs (not shown).

In yet another aspect, the invention relates to a method for engaging material such as a stone for example, a ureteral, urethral, cystic, renal, biliary or gall stone, in a body tract with the laser-resistant fabric retrieval assembly. The laser-resistant fabric retrieval assembly may be positioned close to material to be captured from pockets or difficult-to-access areas of the body, for example, from within the renal calyces. The laser-resistant fabric retrieval assembly is relatively tipless and can make intimate contact with the surface of tissue, even the walls or lining of a pocket-type area, and allows the retrieval of stones and other materials that are unretrievable by conventional tipped baskets that can cause trauma and are limited, by the existence of a protruding tip, in how close the basket can approach the lining of the tissue.

Figure 10B:
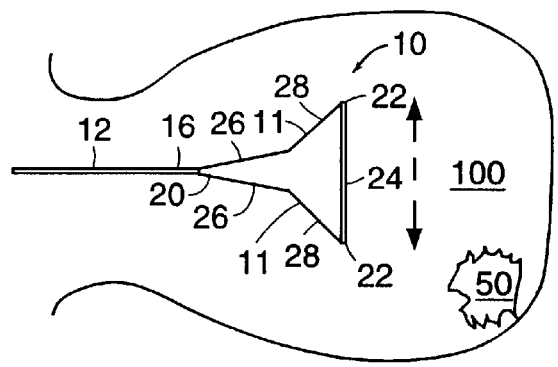
FIG. 10B illustrates a diagrammatic representation of the medical retrieval device in FIG. 10A with a laser-resistant retrieval assembly fully deployed in a renal calyx.
Figure 10C:
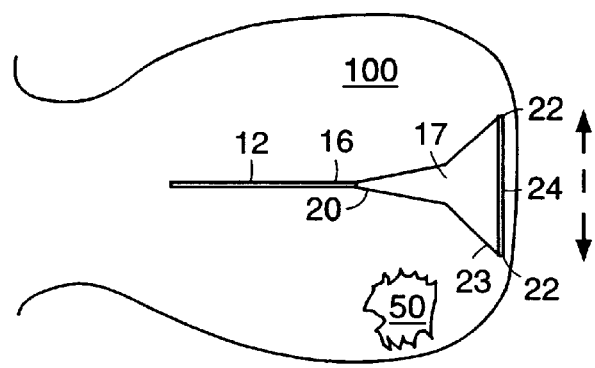
FIG. 10C illustrates a diagrammatic representation of the medical retrieval device in FIG. 10B with the retrieval assembly positioned to capture a stone.

In one embodiment of the invention, a method for engaging material in a body includes inserting a retrieval device 2 having a laser-resistant fabric retrieval assembly 10 into the body, for example, via the ureter 102 into the renal calyx 100 as illustrated in FIG. 10A. In this embodiment, the laser-resistant fabric retrieval assembly serves as a backstop, shield, screen or scraper. Referring still to FIG. 10A, as the device 2 is initially inserted in a patient, the retrieval assembly 10 is in a closed, or collapsed position (also see FIG. 1A) and is completely enclosed within the lumen 14 of the sheath 12. Referring now to FIG. 10B, upon entry of the distal end 16 of the sheath 12 into the renal calyx 100, the laser-resistant fabric retrieval assembly 10 is extended and fully deployed from the distal end 16 of the sheath 12 by maneuvering the fabric retrieval assembly 10 via one or more actuators 4 on the handle 8 (not shown) or by maneuvering the sheath 12 by one or more actuators 4 on the handle 8. As illustrated in FIG. 10B, in the fully-deployed configuration, the proximal portion 26 and distal portion 28 of the legs of the retrieval assembly 10 extend beyond the distal end 16 of the sheath 12. In this configuration, the distal ends 22 of the legs 11 are parted at a maximal distance "1" and the laser-resistant fabric 24 attached to the distal end 22 of the legs 11 is stretched flat and taut. Referring now to FIG. 10C, the edge 23 of the taut, flat laser-resistant fabric 24 is used to scoop the stone 50 into the space 17 located between the distal end 16 of the sheath and the fabric 24.

Figure 10D:
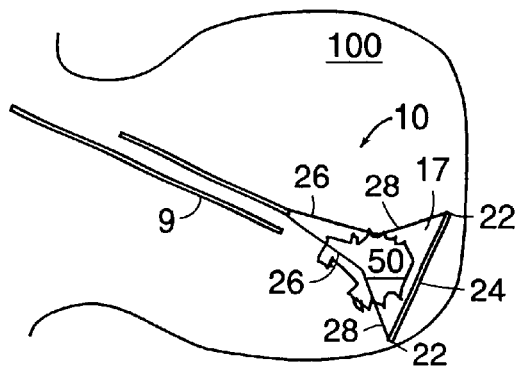
FIG. 10D illustrates a diagrammatic representation of the retrieval device in FIG. 10C with the stone captured by the fully deployed laser-resistant retrieval assembly and a lithotriptor adjacent the stone.

Once the stone 50 is engaged by the fabric retrieval assembly 10 and positioned between the end of the sheath 16 and the fabric 24 in the space 17, a laser or other form of lithotriptor 9 can be positioned near the stone 50 as shown in FIG. 10D. Referring to FIG. 10D, in this embodiment, the fabric 24 serves as a backstop, shield, filter, or screen for the stone 50 while it is being fragmented by the lithotriptor 9. The lithotriptor, preferably a laser lithotriptor, is inserted through the medical device as illustrated in FIG. 10D and positioned near the stone 50. Alternatively, the lithotriptor 9 is introduced via a separate device as previously illustrated in FIG. 1D.

Referring to FIG. 10E, once the stone 50 is fragmented by the lithotriptor 9 and while the fabric retrieval assembly 10 is fully-deployed, the edge 23 of the fabric 24 can be used to guide the fragmented stones closer to the orifice 104 of the body tract 102 to aid in their elimination from the body.

Another embodiment of this aspect of the invention includes a method for engaging material in a body tract by capturing the material. In this embodiment, the retrieval device is inserted into the body tract 100 of a patient while the fabric retrieval assembly 10 is enclosed within the sheath (not shown). In the next step, just the distal portion 28 of the legs 11 of the retrieval assembly 10 is positioned beyond the distal end of the sheath 16 by maneuvering one or more actuators on the handle to move the sheath and retrieval assembly relative to one another. Thus, as previously illustrated in FIGS. 3A and 3B, the fabric retrieval assembly assumes a convex shape. This configuration of the fabric retrieval assembly 10 can be achieved either by moving the retrieval assembly 10 from the closed position to the partially deployed position wherein the proximal portion 26 of the legs 11 remain enclosed within sheath 12, best illustrated in FIGS. 1A and 9A, or by moving the fabric retrieval assembly 10 from the fully deployed position, wherein the distal portion 28 and the proximal portion 26 of the legs 11 are fully extended beyond the distal end 16 of the sheath 12, to the partially deployed convex position, best illustrated in FIGS. 2A, 2B and 6A, 6B.

Figure 11A:
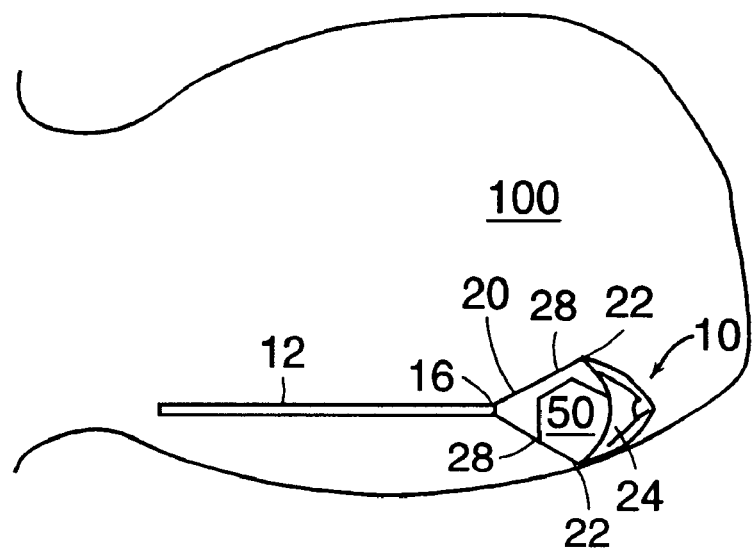
FIG. 11A illustrates a diagrammatic representation of a stone captured in the interior of a partially deployed, convex laser-resistant retrieval assembly positioned in the lumen of a renal calyx.
Figure 11B:
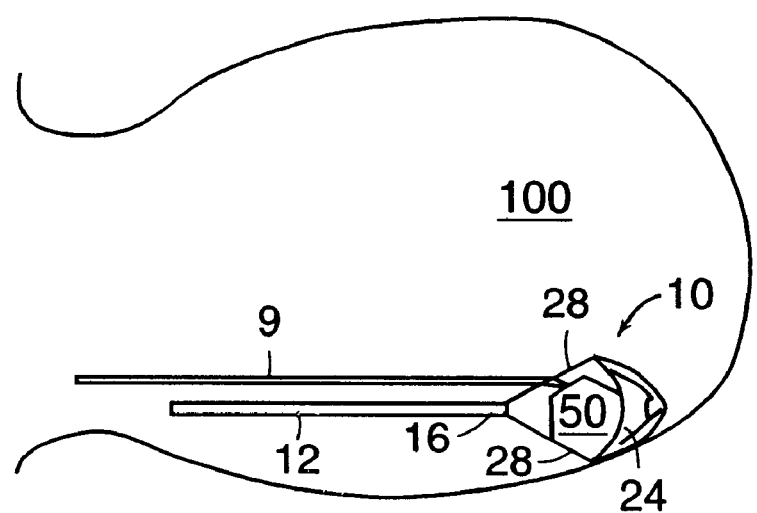
FIG. 11B illustrates a diagrammatic representation of the retrieval assembly in FIG. 11A and a lithotriptor approaching the captured stone.

Next, with the laser-resistant retrieval assembly 10 in the convex-shaped configuration, stone 50 or stone fragments are engaged by the laser-resistant retrieval assembly 10 as illustrated in FIG. 11A. The distal portion 28 of the legs 11 may be drawn at least partially within the lumen 14 of the distal end of the sheath 12 by advancing the sheath 12 over the distal portion 28 or by withdrawing the legs 11 into the lumen 14 of the sheath 12, thereby collapsing the convex retrieval assembly about the captured stone 50 to tightly engage the stone 50. With the stone 50 or stone fragments captured within the convex laser-resistant retrieval assembly 10, the stone 50 or stone fragments are removed from the body by withdrawing the medical retrieval device from the body. As illustrated in FIG. 11B, a stone 50 captured within the convex-shaped laser-resistant retrieval assembly 10 could also be fragmented by a lithotriptor 9.

In some cases, the stone 50 captured within the retrieval assembly 10 in the convex position shown in FIG. 11A, may be too large to be removed through the orifice of the body tract. If the stone 50 is too large to be removed, the retrieval assembly 10 can be fully deployed from the distal end 16 of the sheath 12 by extending the distal portion 28 and the proximal portion 26 of the legs 11 of the retrieval assembly 10 beyond the distal end 16 of the sheath 12 to maximally extend the distance "1" between the parted ends 22 of the legs 11 as illustrated previously in FIG. 11A. In this configuration, the size of the retrieval assembly is maximal, allowing for easy removal of the stone 50 from the lumen of the retrieval assembly 10. Alternatively, the stone 50 or stone fragments can be repositioned, while engaged by the convex retrieval assembly, to another site in the body where the stone is more accessible to surgical intervention.

In another method of the invention, the convex-shaped fabric retrieval assembly can also be used as a backstop, screen, shield, or filter. Referring to FIG. 11C, for example, the medical retrieval device 2 is inserted into a body tract 102. The distal end of the sheath 16 is positioned beyond the stone 50. Referring to FIG. 11D, the retrieval assembly 10 is partially deployed from the distal end 16 of the sheath 12, i.e., only the distal portion 28 of the legs 11 of the retrieval assembly 10 extend beyond the distal end 16 of the sheath 12. Thus, the retrieval assembly 10 assumes a convex configuration as shown in FIG. 11D. The stone 50 is fragmented by a lithotriptor 9 as illustrated in FIG. 11E. With the convex retrieval assembly 10 distal to the stone 50, the retrieval assembly 10 serves as a backstop or filter for the stone fragments thereby preventing the stone fragments from advancing more distally in the body tract. The stone fragments can be removed from the body in the retrieval assembly as the medical device is withdrawn from the body or the stone fragments can be left within the body tract to be naturally eliminated from the body.

Figure 12A:
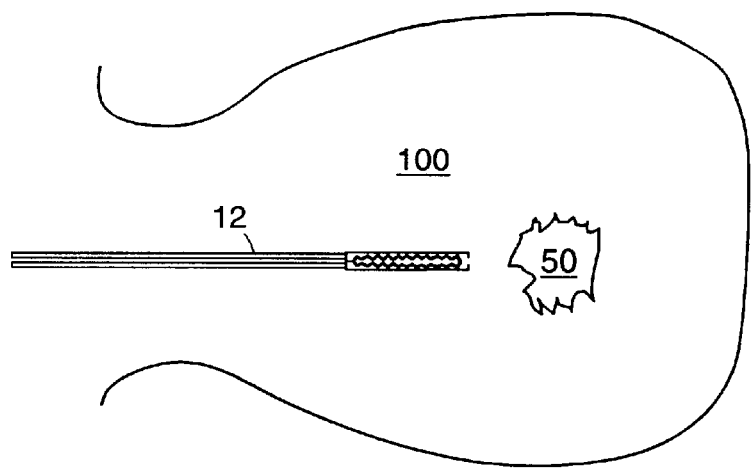
FIG. 12A illustrates a diagrammatic representation of a retrieval assembly in the collapsed position according to the invention approaching a stone in the renal calyx.
Figure 12B:
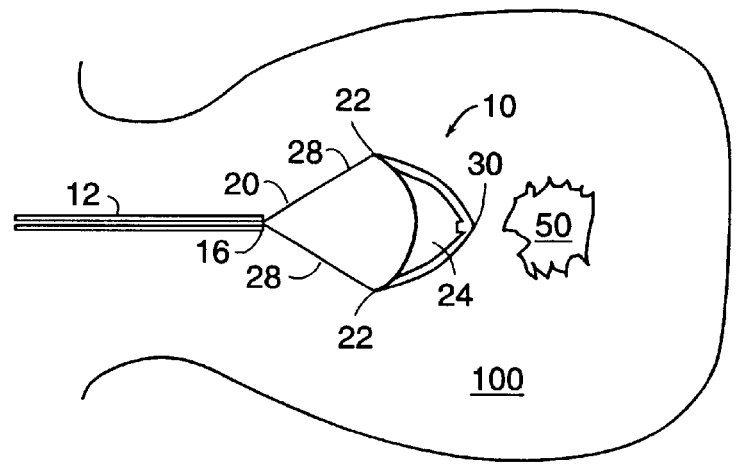
FIG. 12B illustrates a diagrammatic representation of the retrieval assembly illustrated in FIG. 12A in a partially deployed position.
Figure 12C:
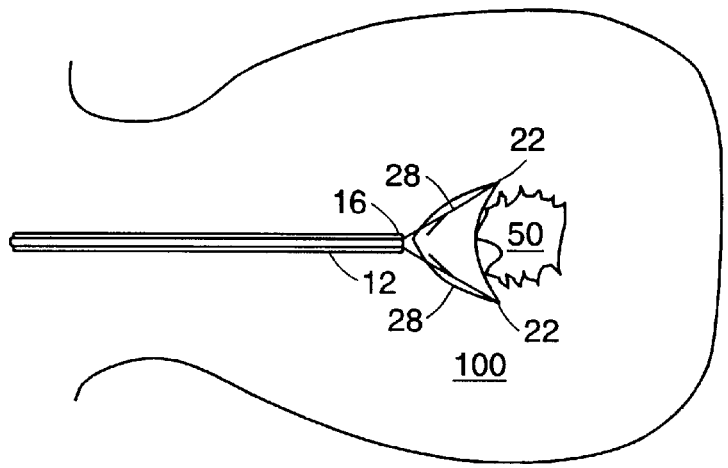
FIG. 12C illustrates a diagrammatic representation of the retrieval assembly illustrated in FIG. 12A and FIG. 12B, with the retrieval assembly in a concave configuration and a stone captured by the retrieval assembly.

Another embodiment of the invention includes a method for engaging material, such as a stone, within the body wherein the fabric laser-resistant retrieval assembly is a grasping or forceps-like retrieval assembly. In this embodiment, the medical retrieval device 6 is first inserted in the body 100, such as into the renal calyx, with the fabric retrieval assembly 10 enclosed within the sheath 12, as illustrated in FIG. 12A. Next, the retrieval assembly 10 is partially deployed from the sheath 12, as illustrated in FIG. 12B, to assume the convex-shaped, grasping or forceps-like retrieval assembly configuration described above. In this configuration, only the distal portion 28 of the legs 11 of the fabric retrieval assembly 10 extends beyond the distal end 16 of the sheath 12. In the next step, the outside of the convex shaped laser-resistant fabric 24, i.e. the apex 30 of the fabric 24, is pushed against the stone 50 causing the fabric 24 to invert forming a concave, or grasper, or forceps-like configuration. The stone 50 is thereby grasped within the concave fabric 24. The stone 50 can be gripped more tightly within the concave fabric 24 by partially withdrawing the retrieval assembly 10 into the lumen 14 of the sheath 12 by advancing the sheath over the distal portion 28 of the legs 11, or withdrawing at least a portion of the distal portion 28 of the legs into the lumen 14 of the sheath 12. The stone 50, grasped by the fabric retrieval assembly 10, can be removed from the body as the medical retrieval device is withdrawn from the body. Alternatively, the stone can be repositioned by the retrieval assembly to another site in the body that is more accessible to laser therapy or other forms of medical/surgical intervention. The stone can be released from the concave grasper fabric retrieval assembly if the stone is too large to be manipulated in the body tract. The stone can also be fragmented by a lithotriptor, such as a laser lithotriptor. The lithotriptor can be inserted through the medical device as illustrated in FIG. 1C or may be introduced via another, separate medical device as shown in FIG. 1D.

Referring to FIG. 13A, by way of example, in another embodiment of the invention, the medical retrieval device includes at least one of many retrieval assembly designs that include a plurality of legs or loops, described below in greater detail, for engaging material within a body, in which at least a portion of the retrieval assembly includes a substance that is resistant to damage induced by laser energy.

At least one substance that has properties that resist damage induced by laser energy is used in the manufacture of at least a portion of the retrieval assembly. Some of the laser resistant materials that may be used are fluorocarbon plastics such as expanded polytetrafluoroethylene (EPTFE), polytetrafluoroethylene (PTFE), tetrafluoroethylene (TFE), fluorinated ethylenepropylene (FEP), perfluoroalkoy (PFA), ethylene tetra-fluoroethylene (ETFE), polyvinylidene fluoride (PVDF)|. The laser-resistant material can also be ceramics or gold, silver or nickel plating polished to a reflective surface, or any material that is resistant to damage induced by laser energy. As illustrated in FIG. 13A, the laser resistant substance can be incorporated in the materials used to manufacture the retrieval assembly. As illustrated in FIGS. 13A, 13B, 14A, 14B, 15A and 15B, all or a portion of the laser-resistant retrieval assembly can be manufactured from materials incorporating laser-resistant substances, or one or more of the legs, loops or other components of a retrieval assembly can be manufactured from at least one substance that resists laser energy-induced damage.

In a typical retrieval assembly, illustrated in FIG. 13A, legs 11a and 11b include at least one laser-resistant substance throughout their entire length, i.e., from the proximal end 40 to the distal end 42 of the legs 11a and 11b. Cross-sections of the retrieval assembly at levels (a), (b), and (c) are shown in FIG. 13B. Cross-hatching represents the presence of at least one laser-resistant substance.

In another embodiment of the invention, referring now to FIG. 14A, legs 11a, 11b, 11c and 11d include at least one laser-resistant substance throughout their length, i.e., from the proximal end 40 to the distal end 42 of the legs 11. Cross-sections of the retrieval assembly at levels (a), (b), and (c) are shown in FIG. 14B.

In an alternate embodiment, referring to FIG. 15A, a portion of each of the legs 11a, 11b, 11c and 11d of retrieval assembly 10 include at least one laser-resistant substance. Referring now to FIG. 15B at levels (a) and (b), but not (c), legs 11a, 11b, 11c and 11d include at least one laser-resistant substance.

The illustrated retrieval assembly, combinations of legs or loops, and portions of legs or loops that include at least one laser resistant substance, are meant to be illustrative and not limiting as to other types of retrieval assemblies that include at least one laser-resistant substance, possible combination of legs or loops, or portions of legs or loops that include at least one laser-resistant substance.

Figure 16A:
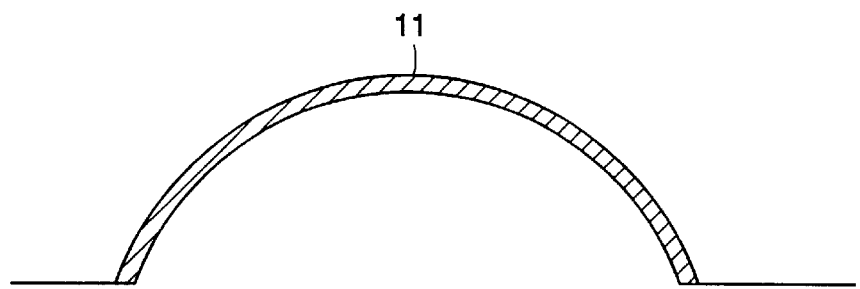
FIG. 16A illustrates a side-view of a leg of a retrieval assembly coated with at least one substance resistant to laser energy-induced damage.
Figure 16B:
FIG. 16B illustrates an embodiment of a cross-section of the leg of the retrieval assembly illustrated in FIG. 16A.

In another embodiment, according to the invention, at least a portion of the retrieval assembly is covered with a substance that has properties that resist damage induced by laser energy, i.e., one or more portions of a retrieval assembly are covered on the surface with a laser-resistant material. Such materials include fluorocarbon plastics such as expanded polytetrafluoroethylene (EPTFE), polytetrafluoroethylene (PTFE), tetrafluoroethylene (TFE), fluorinated ethylenepropylene (FEP), perfluoroalkoy (PFA), ethylene tetra-fluoroethylene (ETFE), polyvinylidene fluoride (PVDF). The laser resistant material can also be ceramics or gold, silver or nickel plating polished to a reflective surface. A typical retrieval assembly leg is shown in FIG. 16A. In this embodiment, a leg 11 is covered with a laser-resistant substance (represented by cross-hatching) along the entire length of the leg 11. In another embodiment, the entire circumference of the leg, illustrated by a cross-section of a leg in FIG. 16B, is covered with at least one substance that resists laser energy-induced damage. In another embodiment, only a portion of the circumference of the leg, illustrated in FIG. 16C, is covered with at least one substance that resists laser energy-induced damage.

Figure 16C:
FIG. 16C illustrates another embodiment of a cross-section of a leg of the retrieval assembly illustrated in FIG. 16A.
Figure 20A:
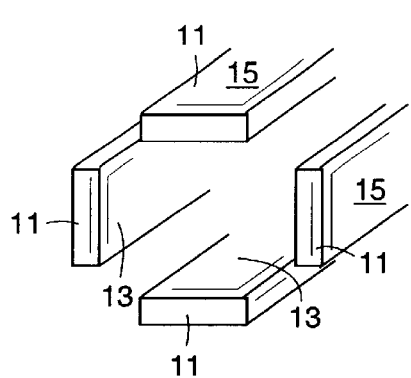
FIG. 20A illustrates cross-sections of four rectangular legs of a laser-resistant retrieval assembly.
Figure 20B:
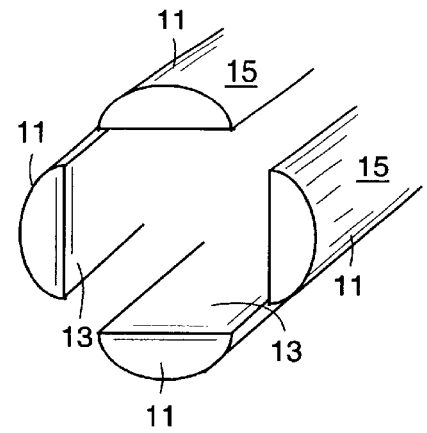
FIG. 20B illustrates cross-sections of four D-shaped legs of a laser-resistant retrieval assembly.
Figure 20C:
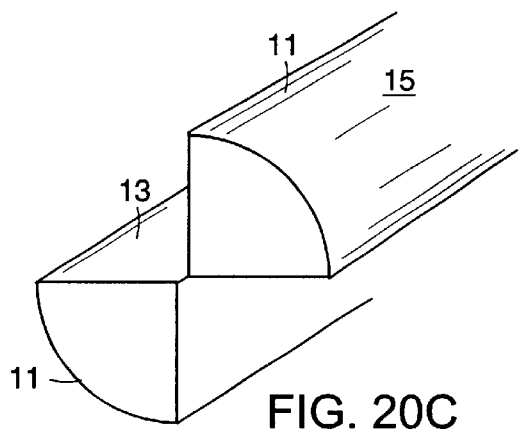
FIG. 20C illustrates cross-sections of two V-shaped legs of the laser-resistant retrieval assembly.
Figure 20D:
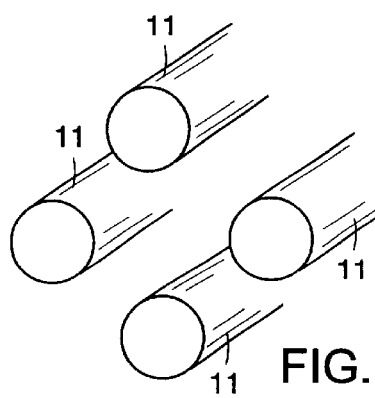
FIG. 20D illustrates a cross-section of a round leg of the laser-resistant retrieval assembly.
Figures 20E, 20F:
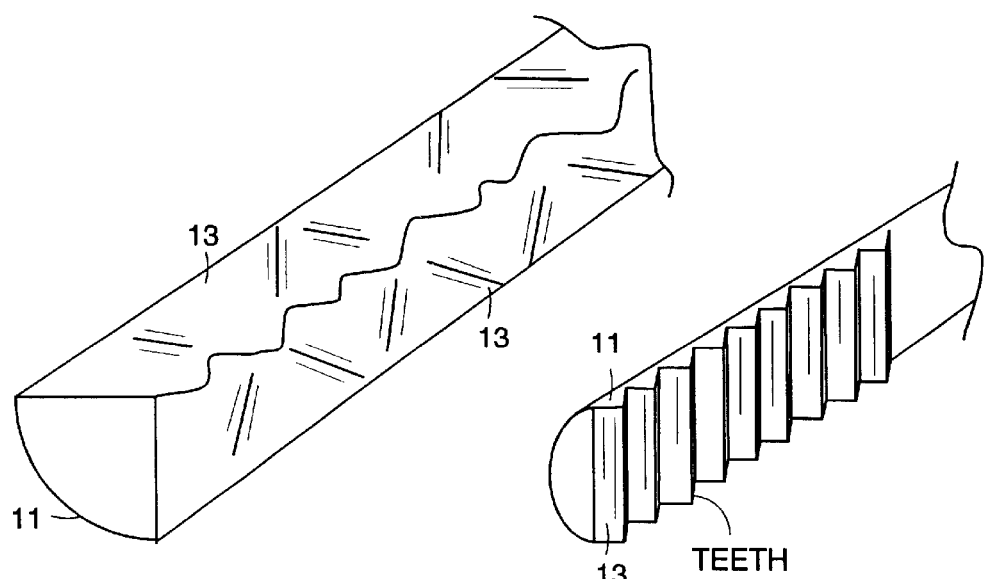
FIG. 20E illustrates a cross-section of a D-shaped leg having teeth on the inner surface of the leg.
FIG. 20F illustrates a cross-section of a V-shaped leg of the laser resistant retrieval assembly having teeth with sharpened cutting edges located on the inner surface of the leg.

The part of the leg of the retrieval assembly illustrated in FIGS. 16B and 16C covered by at least one substance resistant to laser energy-induced damage is meant to be illustrative and not limiting to the part of the leg that is coated with the laser-resistant substance.

The legs of the retrieval assembly are covered with the laser-resistant substance by any means known in the art, for example, by dipping, painting, spraying, or by the application of a sleeve comprising at least one laser-resistant material over the part of the retrieval assembly. The sleeve can be, for example, 0.001 inches thick. The sleeve ends are secured to the retrieval assembly with a cyanoacrylate adhesive. An expanded PTFE sleeve will withstand holmium laser energy hits in the range of 0.6 to 1.0 joule.

Referring to FIG. 17A, at least a portion of the retrieval assembly, according to the invention, is covered with at least one substance that has properties that are resistant to laser energy-induced damage. One or more of the legs, loops, or other components of a retrieval assembly are covered with at least one substance having properties that resist laser energy-induced damage. In a typical retrieval assembly 10, as illustrated in FIG. 17A, legs 11a and 11b are covered with at least one substance that has properties that resist damage induced by laser energy throughout their entire length from the proximal end 40 to the distal end 42 of the legs 11a and 11b. Cross-sections of the retrieval assembly 10 at levels (a), (b), and (c) are shown in FIG. 17B.

In another embodiment of the invention, referring now to FIG. 18A, legs 11a, 11b, 11c and 11d are covered throughout their entire length from the proximal end 40 to the distal end 42 of legs 11a, 11b, 11c, 11d with at least one substance that has properties that resist damage induced by laser energy. Cross-sections of the retrieval assembly 10 at levels (a), (b) and (c) are illustrated in FIG. 18B.

In an alternate embodiment, referring now to FIG. 19A, a portion of each of the legs 11a, 11b, 11c, and 11b of the retrieval assembly 10 include at least one laser-resistant substance. Referring to FIG. 19B, legs 11a, 11b, 11c, and 11d, at levels (a) and (b), but not level (c) are covered with at least one laser resistant substance.

The illustrated retrieval assembly, combinations of legs or loops, and portions of legs or loops covered with at least one substance having properties that are resistant to laser energy-induced damage, are meant to be illustrative and not limiting as to other types of retrieval assemblies that are covered with at least one laser-resistant substance, possible.

Laser-resistant retrieval assemblies according to the invention, in addition to the retrieval assemblies with round legs illustrated in FIGS. 13A–19B, can also include at least one substance having properties that are resistant to laser energy-induced injury. Referring to FIGS. 20A–20F, such retrieval assemblies have legs 11 that are, for example, rectangular (FIG. 20A), D-shaped (FIG. 20B), V-shaped (FIG. 20C), or B-shaped (not shown). Retrieval baskets including these features are described in U.S. Ser. No. 09/027,534, the entirety of which is incorporated by reference herein. The legs of the retrieval assembly can have more than one surface such as an inner surface 13 and an outer surface 15. The inner surface 13 can be roughened by, for example, teeth, as illustrated on a D-shaped leg in FIG. 20E or by cutting edges as illustrated on a V-shaped leg in FIG. 20F. Any portion of a leg illustrated in FIGS. 20A–20F can include at least one substance that is resistant to laser energy-induced damage. For example, any part of the leg, such as just the inner surface 13 or just the outer surface 15, may be covered with a laser-resistant substance.

Figure 21A:
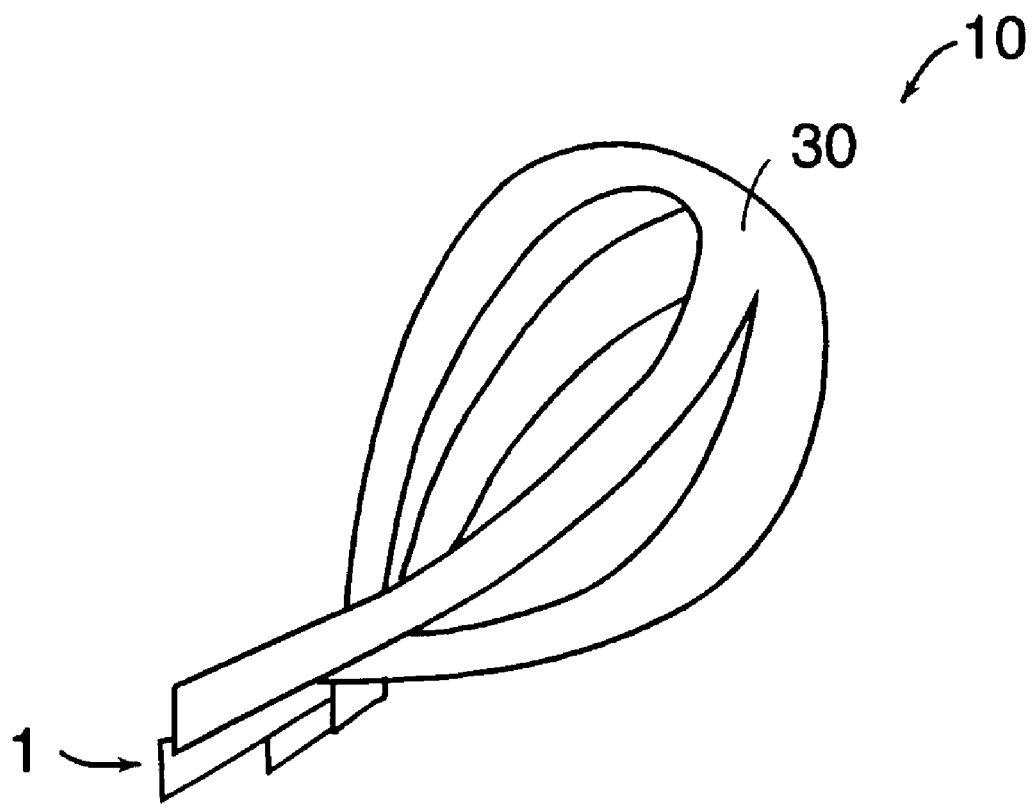
FIG. 21A illustrates a side view of an embodiment of a laser-resistant retrieval assembly according to the invention including an atraumatic distal tip.
Figure 21B:
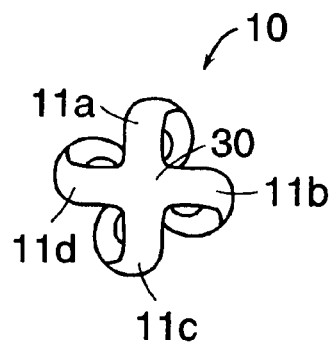
FIG. 21B illustrates an end view of the retrieval assembly in FIG. 21A.
Figure 21C:
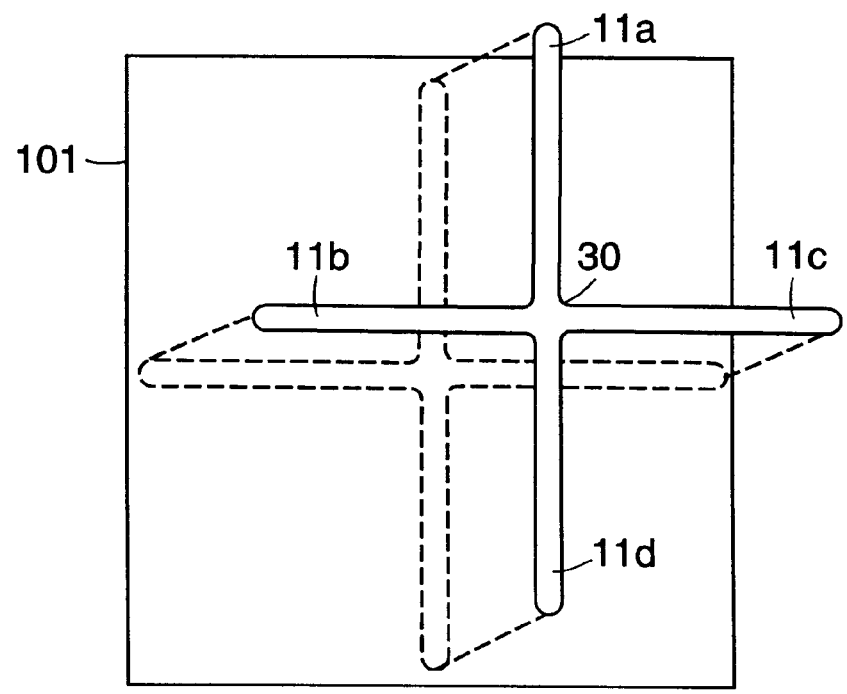
FIG. 21C illustrates a top view of an X-profile embodiment of at least a distal end portion of a laser-resistant retrieval assembly removed from a single piece of substantially flat material according to the invention.

In another embodiment of the invention, illustrated in FIG. 21A, the distal end 30 of the retrieval assembly 10 is tipless or atraumatic. Retrieval baskets including these features are described in U.S. Ser. No. 09/296,327, the entirety of which is incorporated by reference herein, and U.S. Ser. No. 09/268,484, the entirety of which is incorporated by reference herein. The distal end portion 30 of the retrieval assembly is defined by a shape which comprises a single continuous unit manufactured from a single piece of substantially flat material. For example, as illustrated in a side-view in FIG. 21B and an end-view in FIG. 21C, the tipless retrieval assembly 10 is manufactured from a single sheet of material. In this embodiment, a shape with legs 11a, 11b, 11c, 11d, as illustrated in FIG. 21C, is removed from the single sheet of material 101. The retrieval assembly 10 is contoured to form the shape of at least a portion of the distal end of a retrieval assembly by heat shaping, cold forming, or by other processes known in the art, the shape removed from the single piece of material. The sheet of material can include at least one substance that is resistant to laser energy-induced damage. Alternatively, at least one laser energy resistant substance can be applied to one or more surfaces of the sheet of material, such as the top surface shown in FIG. 21C. The laser energy resistant substance can be applied before the shape is removed from the single piece of material, or the laser energy resistant substance can be applied to the retrieval assembly after the retrieval assembly is removed from the single piece of material.

Figure 22A:
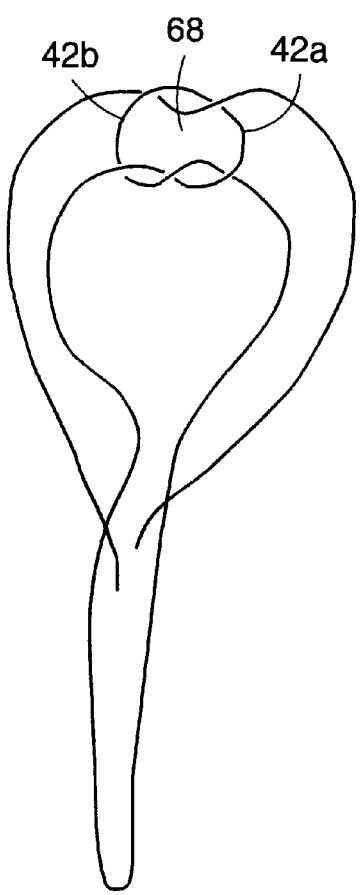
FIG. 22A illustrates an embodiment of a laser-resistant retrieval assembly according to the invention including a knotted tip.
Figure 22B:
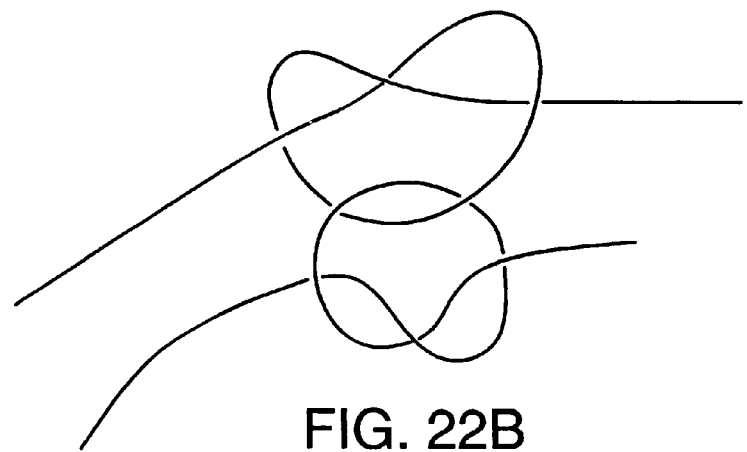
FIG. 22B illustrates another embodiment of a distal portion of a laser-resistant retrieval assembly according to the invention including a knotted tip.

Referring to FIGS. 22A and 22B, another embodiment of an atraumatic laser-resistant retrieval assembly includes a retrieval assembly having a plurality of legs that are knotted at the distal end 30 of the retrieval assembly 10. At least a portion of the atraumatic retrieval assembly illustrated in FIG. 22A or FIG. 22B includes a substance resistant to damage from laser energy. Other embodiments of a retrieval assembly having a plurality of legs that are knotted at the distal end of the retrieval assembly are also possible and are not limited to the embodiments illustrated in FIGS. 22A and 22B.

Figure 23:
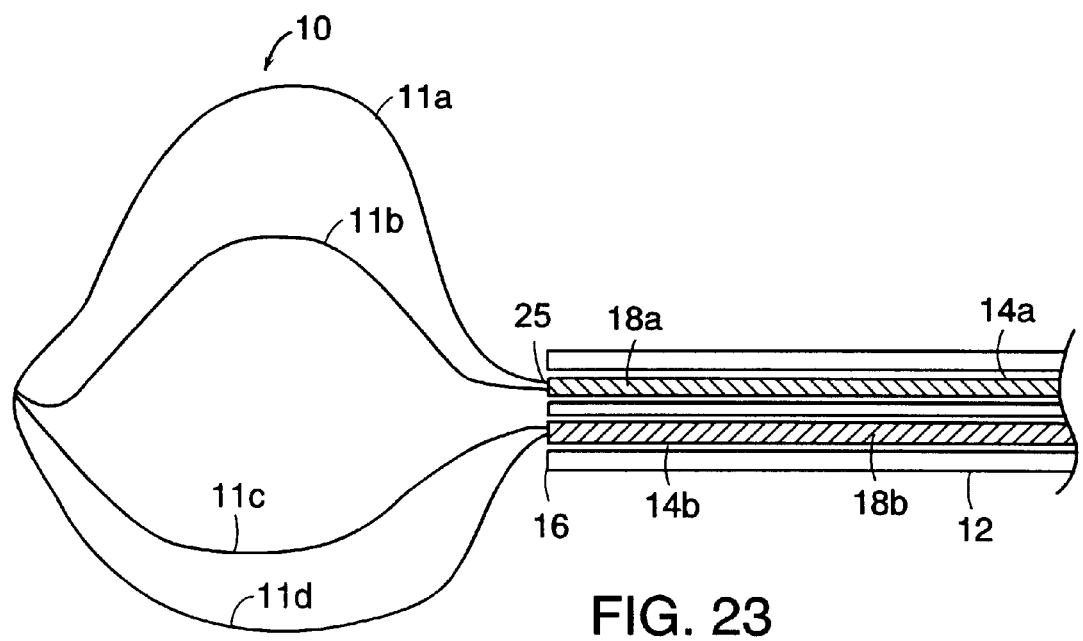
FIG. 23 illustrates an embodiment of a laser-resistant retrieval assembly according to the invention, including at least one individually actuateable leg.

In another embodiment, the laser-resistant retrieval assembly has at least one individually actuateable leg. Retrieval assemblies having these features are described in U.S. Ser. No. 09/065,158, the entirety of which is incorporated by reference herein. As illustrated in FIG. 23, in this embodiment, at least one of the legs of the laser-resistant retrieval assembly is independently moveable from at least one of the other legs. Thus, when the retrieval assembly is maneuvered to capture a stone in the lumen of the retrieval assembly, at least one leg can be actuated independently to adjust the distance in the gap between the legs. Once the stone is captured, the independently actuateable leg can be adjusted again to retain the stone in the lumen of the basket.

In the embodiment of a medical retrieval device having at least one individually actuateable leg, one or more lumens can extend axially in a sheath with at least one elongated member disposed within each lumen, the elongated member being operably attached to at least one actuator in the handle (not shown). The proximal end of at least one leg is operably attached to the distal end of at least one elongated member.

For example, referring to FIG. 23, two legs 11a and 11b, in a four-leg laser-resistant retrieval assembly 10 are operably attached to the distal end of a first elongated member 18a. The remaining two legs, 11c and 11d, of the retrieval assembly 10 are operably attached to a second elongated member 18b. Elongated member 18a is enclosed within sheath lumen 14a and elongated member 18b is enclosed within a separate sheath lumen 14b. When the first elongated member 18a is advanced towards the distal end 16 of the sheath 12, the legs 11a and 11b hyperextend from the distal end 16 of the sheath 12. The retrieval assembly 10 assumes an asymmetrical shape, as illustrated in FIG. 22A, as the legs 11a and 11b attached to the elongated member 18a are hyperextended. At least a portion of the retrieval assembly having at least one individually actuateable leg includes a substance that is resistant to laser energy-induced damage.

Other combinations of actuateable legs, sheath lumens and elongated members are possible and the invention is not limited to the embodiment illustrated in FIG. 23.

Figure 24A:
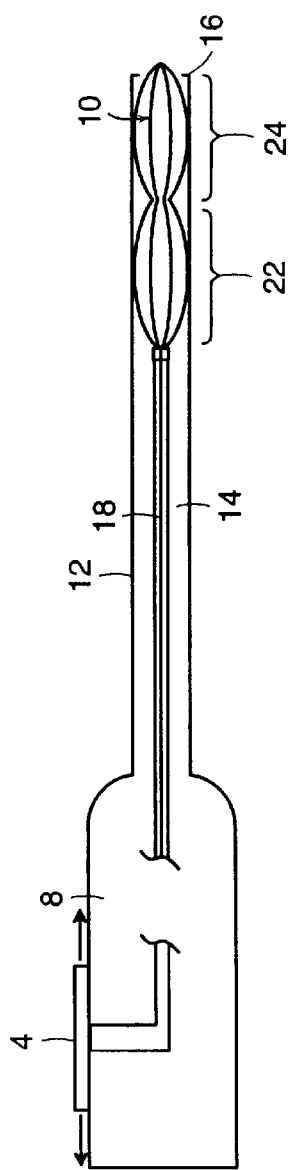
FIG. 24A illustrates an embodiment of a laser-resistant retrieval assembly according to the invention having multiple retrieval assembly portions enclosed within the sheath.
Figure 24B:
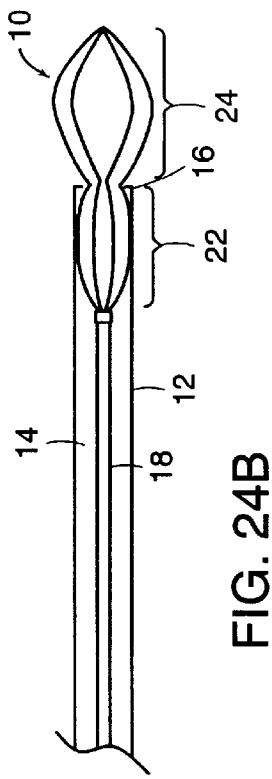
FIG. 24B illustrates a portion of the retrieval assembly illustrated in FIG. 24A partially deployed from the sheath.
Figure 24C:
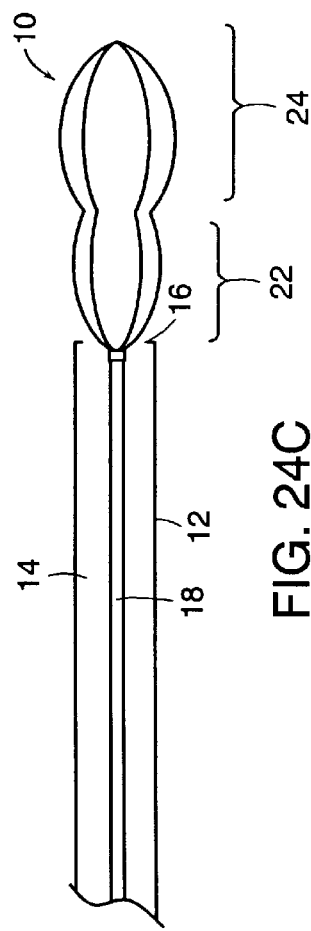
FIG. 24C illustrates all portions of the retrieval assembly illustrated in FIG. 24A fully deployed from the sheath.

Also, in another embodiment, the laser-resistant assembly retrieval assembly 10 can have at least two portions, for example, a proximal portion 22 and a distal portion 24 as shown, for example, in FIGS. 24A–24C. Retrieval assemblies having these features are described in U.S. Ser. No. 09/369,269, the entirety of which is incorporated by reference herein. Each of the proximal and distal portions of the retrieval assembly 10 can assume a variety of shapes such as, for example, a bulbous shape or a wedge shape. The distal portion 24 of the retrieval assembly is for capturing material, as shown in FIG. 24B, when the distal portion 24 is extended beyond the distal end 16 of the sheath 12 and the proximal portion 22 is enclosed within the lumen 14 of the sheath 12. Referring now to FIG. 24C, material captured within the interior of the retrieval assembly 10 can be released from the retrieval assembly 10 by extending the proximal portion 22 of the retrieval assembly 10 as well as the distal portion 24 of the retrieval assembly 10 from the distal end 16 of the sheath 12.

As described above, portions or all of the retrieval assembly having multiple portions can include a substance resistant to laser energy-induced damage or portions or all of the retrieval assembly can be covered with a substance that is resistant to laser energy-induced damage.

Figure 25:
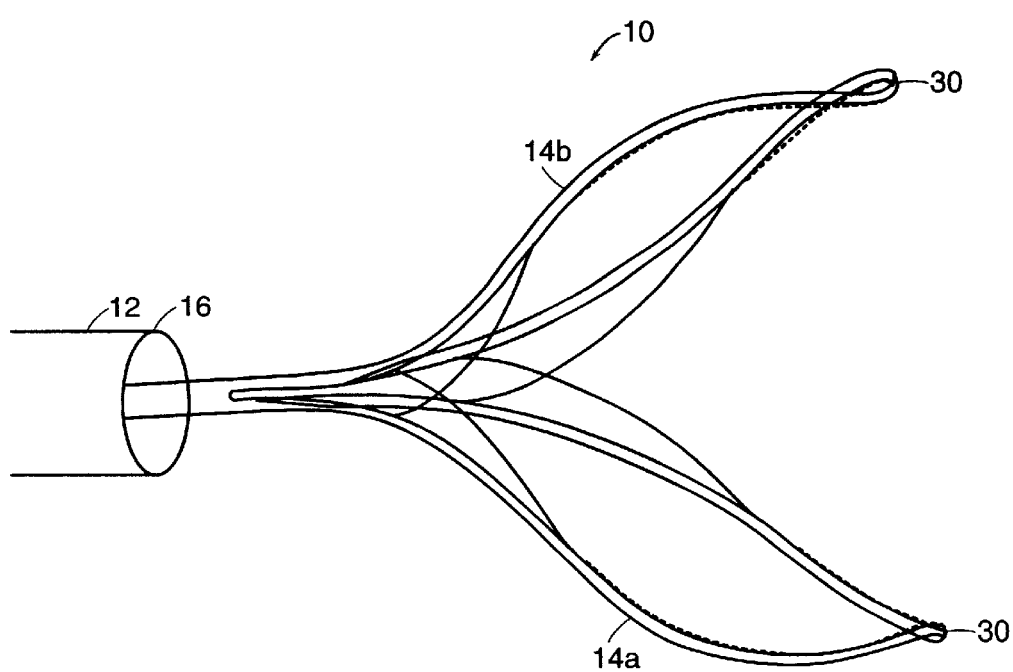
FIG. 25 illustrates an embodiment of a laser-resistant retrieval assembly according to the invention having a plurality of opposing loops.

In yet another embodiment of the laser-resistant retrieval device, the laser resistant retrieval assembly is formed by a plurality of loops. Retrieval assemblies having these features are described in U.S. Ser. No. 09/064,704, the entirety of which is incorporated by reference herein. Referring to FIG. 25, in a two loop embodiment, the loops 14a, 14b are joined at the base 20 of the retrieval assembly 10. The distal ends 30 of the loops 14a, 14b are unattached at the distal end of the retrieval assembly 10. One or more loops may be shorter in length than the other loops thereby enabling one loop to pass through the lumen of another loop. The retrieval assembly loops 14a, 14b are moveable between a closed position, when the loops of the retrieval assembly are completely enclosed within the distal end of the sheath (not shown), and an open position when the loops 14a, 14b of the retrieval assembly 10 are extended beyond the distal end 16 of the sheath 12 shown in FIG. 25. In the open position, the distal ends 30 of the loops 14a, 14b are parted. In the open position the retrieval assembly 10 can be advanced over material, such as a stone in a body tract. With the loops of the retrieval assembly parted in the open position, the retrieval assembly can be advanced directly over the stone in front of the retrieval assembly to end-encapsulate the stone, or the stone can be approached from the side of the retrieval assembly and side-encapsulated.

As described above, portions or all of the loop retrieval assembly can include a substance resistant to laser energy-induced damage or portions or all of the loop retrieval assembly can be covered with a substance that is resistant to laser energy-induced damage.

Figure 26A:
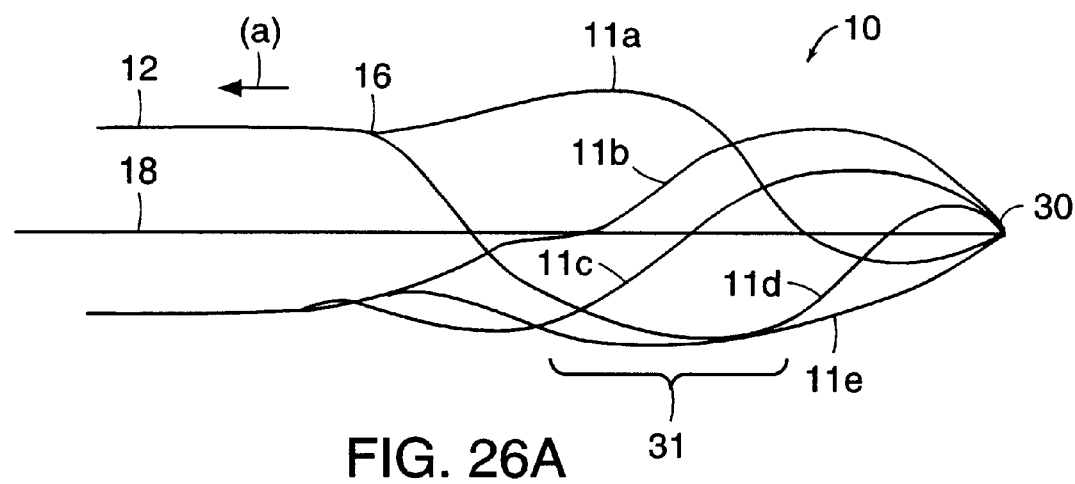
FIG. 26A illustrates an embodiment of a laser-resistant retrieval assembly according to the invention that extends from the wall of the sheath.
Figure 26B:
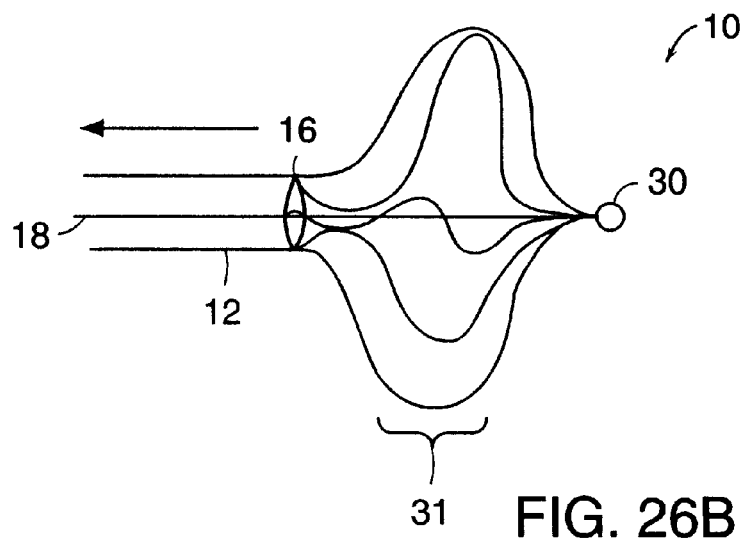
FIG. 26B illustrates the retrieval assembly illustrated in FIG. 26A in an expanded position.

Referring to FIGS. 26a and 26b, in another embodiment of the laser-resistant retrieval assembly, the legs 11a, 11b, 11c, 11d of the retrieval assembly 10 are spiral extensions of or are embedded within the sheath wall at the distal end 16 of the sheath 12. Retrieval assemblies having these features are described in U.S. Pat. No. 5,935,139, the entirety of which is incorporated by reference herein, and U.S. Ser. No. 09/184,135, the entirety of which is incorporated by reference herein. A cannula or elongated member 18 is operably attached to the distal end 30 of the retrieval assembly. As illustrated in FIG. 26b, when the distal end of the retrieval assembly 10 is axially moved in the direction of arrow (a), the distal end 30 of the retrieval assembly 10 is drawn closer to the end 16 of the sheath 12, thereby exerting a compressive force on the retrieval assembly 10. The compressive force on the retrieval assembly 10 causes the retrieval assembly 10 to move between a retracted position illustrated in FIG. 26A and an expanded position illustrated in FIG. 26B. The intermediate portion 31 of the retrieval assembly 10 is displaced radially outward when the retrieval assembly 10 is in the expanded position illustrated in FIG. 26B. The closer the distal portion 30 of the retrieval assembly 10 is brought toward the distend 16 of the sheath 12, the greater is the radial outward displacement of the intermediate portion 31 of the retrieval assembly 10. In accordance with the invention, the retrieval assembly 10 in this position can be used to capture material such as stones in the interior of the retrieval assembly. Alternatively, as described above, the retrieval assembly 10 in the expanded position can be used as a backstop or shield when stones are fragmented by a lithotriptor such as a laser lithotriptor.

As described above, portions or all of the spiral retrieval assembly can include a substance resistant to laser energy-induced damage or portions or all of the spiral retrieval assembly can be covered with a substance that is resistant to laser energy-induced damage.

Variations, modifications, and other implementations of what is described herein will occur to those of ordinary skill in the art without departing from the spirit and the scope of the invention as claimed. Accordingly, the invention is to be defined not by the preceding illustrative description but instead by the scope and spirit of the following claims.

What is claimed is:

1. A medical device comprising:
   a proximal handle;
   a sheath extending distally from the handle and having a lumen; and,
   an engaging assembly for engaging material within a body, the engaging assembly comprising a plumlity of legs, each of the legs having an inside surface and an outside surface, at least a portion of only one of either the inside or the outside surface of at least one leg is covered by a substance resistant to damage from laser energy, the engaging assembly further comprising a position in which the engaging assembly is within the lumen of the sheath and another position in which the engaging assembly extends from a distal end of the sheath and out of the lumen.

2. The medical device of claim 1 wherein said sheath is axially moveable over said engaging assembly, whereby said engaging assembly moves relative to said sheath when said sheath is axially moved.

3. The medical device of claim 1 further comprising an elongated member extending within said sheath lumen and operably attached to a proximal end of said engaging assembly, whereby said engaging assembly moves when said elongated member is axially moved within said sheath.

4. The medical device of claim 1 wherein said engaging assembly comprises a surgical retrieval basket.

5. The medical device of claim 4 wherein said basket comprises a plurality of loops.

6. The medical device of claim 4 wherein said basket comprises an atraumatic tip at the distal end of the basket.

7. The medical device of claim 1 wherein said engaging assembly comprises a single loop configuration.

8. The medical device of claim 1 wherein said engaging assembly is moveable between a closed position and an open position to allow engaging of material in the body.

9. The medical device of claim 1 wherein said engaging assembly comprises a proximal portion and a distal portion, the distal portion for capturing material in a body when the distal end of the sheath and the proximal portion of the engaging assembly is collapsed within the sheath, the engaging assembly expanding to release captured material when the distal and proximal portions of the engaging assembly extend from the distal end of the sheath.

10. The medical device of claim 1 wherein said engaging assembly comprises a grasper, said grasper comprising a plurality of opposing loops and having a collapsed position in which the loops are collapsed within the lumen of the sheath and another position in which at least a portion of the loops extend from the distal end of the sheath and out of the lumen, the loops being joined at a base and unattached to each other at their distal ends, the loops being moveable between an open position and a closed position with the loops being closer together at their distal ends when in the closed position than when in the open position to allow capture and release of material.

11. The medical device of claim 10 wherein said grasper comprises two opposing loops.

12. The medical device of claim 1 wherein said engaging assembly comprises a surgical screen.

13. The medical device of claim 1 wherein said substance comprises at least one fluorocarbon plastic.

14. The medical device of claim 13 wherein said fluorocarbon plastic comprises expanded polytetrafluoroethylene.

15. The medical device of claim 13 wherein said fluorocarbon plastic comprises polytetrafluoroethylene.

16. The medical device of claim 13 wherein said fluorocarbon plastic comprises tetrafluoroethylene.

17. The medical device of claim 13 wherein said fluorocarbon plastic comprises fluorinated ethylenepropylene.

18. The medical device of claim 13 wherein said fluorocarbon plastic comprises perfluoroalkoy.

19. The medical device of claim 13 wherein said fluorocarbon plastic comprises ethylene tetra-fluoroethylene.

20. The medical device of claim 13 wherein said fluorocarbon plastic comprises polyvinylidene fluoride.

21. The medical device of claim 1 wherein said substance comprises a ceramic, gold, silver, or nickel.

22. The medical device of claim 1, wherein at least one of said legs is actuateable.

23. A medical device comprising:

a proximal handle;

a sheath extending distally from the handle and having a lumen;

an engaging assembly for engaging material within a body, the engaging assembly comprising a plurality of legs, each of the legs having an inside surface and an outside surface, at least a portion of one of the inside and the outside surface of at least one leg is covered by a substance resistant to damage from laser energy, the engaging assembly further comprising a position in which the engaging assembly extends from a distal end of the sheath and out of the lumen; and a lithotriptor extending through said sheath.

\* \* \* \* \*